(12) United States Patent
Zhu et al.

(10) Patent No.: US 6,936,416 B2
(45) Date of Patent: Aug. 30, 2005

(54) EXPRESSION MONITORING FOR HUMAN CYTOMEGALOVIRUS (HCMV) INFECTION

(75) Inventors: Hua Zhu, Newark, NJ (US); Thomas R. Gingeras, Encinitas, CA (US); Thomas Shenk, Princeton, NJ (US)

(73) Assignee: Affymetrix, Inc., Santa Clara, CA (US)

(*) Notice: Subject to any disclaimer, the term of this patent is extended or adjusted under 35 U.S.C. 154(b) by 245 days.

(21) Appl. No.: 09/950,024

(22) Filed: Sep. 12, 2001

(65) Prior Publication Data

US 2004/0014027 A1 Jan. 22, 2004

Related U.S. Application Data

(63) Continuation of application No. 09/377,907, filed on Aug. 20, 1999, now abandoned.
(60) Provisional application No. 60/097,708, filed on Aug. 21, 1998.

(51) Int. Cl.$^7$ .......................... C12Q 1/68; C12P 19/34; C07H 21/04
(52) U.S. Cl. ...................... 435/6; 435/91.1; 435/91.2; 536/23.1; 536/24.3; 536/24.33
(58) Field of Search ....................... 435/6, 91.1, 91.2, 435/5, 235.1; 536/23.1, 24.3, 24.33

(56) References Cited

U.S. PATENT DOCUMENTS

| | | | | |
|---|---|---|---|---|
| 5,273,876 A | * | 12/1993 | Hock et al. ............. | 435/235.1 |
| 5,561,071 A | | 10/1996 | Hollenberg et al. | |
| 5,700,637 A | | 12/1997 | Southern | |
| 5,733,729 A | | 3/1998 | Lipshutz et al. | |
| 5,795,716 A | | 8/1998 | Chee et al. | |
| 5,989,873 A | * | 11/1999 | Vinayagamoorthy et al. ........................ | 435/91.2 |
| 6,124,433 A | | 9/2000 | Falb et al. | |
| 6,607,879 B1 | * | 8/2003 | Cocks et al. ................... | 435/6 |

FOREIGN PATENT DOCUMENTS

WO 89/10977 11/1989

OTHER PUBLICATIONS

Cinque et al., "Cytomegalovirus infections of the nervous system," Intervirology, 1997, vol. 40, No. 2–3, pp. 85–97, Abstract only.*

Zhu et al., "Use of differential display analysis to assess the effect of human cytomegalovirus infection on the accumulation of cellular RNAs: Induction of interferon–responsive RNAs," PNAS, Dec. 1997, vol. 94, pp. 13985–13990.*

Schena et al., "Parallel human genome analysis: Microarray–based expression monitoring of 1000 genes," PNAS, Oct. 199 vol. 93, pp. 10614–10619.*

Soderberg–Naucler et al., "Mechanisms of cytomegalovirus disease," Herpes, 1997, vol. 4, No. 1, pp. 4–9.*

Huey et al., "Altered expression of myosin mRNA and protein in rat soleus and tibialis anterior following reinnervation," America Journal of Physiology—Cell Physiology, 1996, vol. 271, No. 6, pp. C2016–C2026, Abstract only.*

Shibutani et al. "Pertussis Toxin–sensitive G Proteins as Mediators of the Signal Transduction Pathways Activated by Cytomegalovirus Infection of Smooth Muscle Cells" The Journal of Clinical Investigation, vol. 100, No. 8, Oct. 1997 pp. 2054–2061.

Zhu et al. "Cellular gene expression altered by human cytomegalovirus: Global monitoring with oligonucleotide arrays" Proc. Natl. Acad. Sci. USA vol. 95 pp. 14470–14475, Nov. 1998.

Geist and Dai "Cytomegalovirus Modulates Interleukin–6 Gene Expression" Transplantation, vol. 62, No. 5, Sep. 1996, pp. 653–658.

Zhou et al. "Human Cytomegalovirus Increases Modified Low Density Lipoprotein Uptake and Scavenger Receptor mRNA Expression in Vascular Smooth Muscle Cells" The Journal of Clinical Investigation, vol. 98, No. 9, Nov. 1996, pp. 2129–2138.

J. Zhu "Ultraviolet B irradiation and cytomegalovirus infection synergize to induce the cell surface expression of 52–kD/Ro antigen" Clin Exp. Immunol. 1996: 103:47–53.

Boldogh et al. "Novel Activation of γ–Interferon in Nonimmune Cells during Human Cytomegalovirus Replication" Proceedings of the Society for Experimental Biology and Medicine, vol. 215, No. 1, May 1997.

Lois J. Geist et al. "The Immediate Early Genes of Human Cytomegalovirus Upregulate Tumor Necrosis Factor–α Gene Expression" J. Clin. Invest. vol. 93, Feb. 1994, pp. 474–478.

Colberg–Poley and Santomenna "Selective Induction of Chromosomal Gene Expression by Human Cytomegalovirus" Virology, 1988, vol. 166, pp. 217–228.

Zhu et al. Use of Differential Display and DNA Array Technology to Assess the Effect of Human Cytomegalovirus Infection on Signal Transeduction pathways. FASEB Journal, Apr. 1998, vol. 12, No. 8, p. A1308.

(Continued)

Primary Examiner—Kenneth R. Horlick
Assistant Examiner—Young J. Kim
(74) Attorney, Agent, or Firm—Banner & Witcoff, Ltd.

(57) ABSTRACT

Certain human genes have been found to be induced or repressed in host cells infected with HCMV. A large set of such genes has been identified. These have diagnostic use in determining the extent of tissue damage caused by the infection as well as in determining the stage of disease progression of the HCMV infection. Such genes are likely those involved in mediating the pathology of the infected tissues. Thus by identifying agents which are able to reverse the induction or repression of such genes, one can find candidate therapeutic agents for use in treating and or preventing HCMV-caused disease pathologies.

29 Claims, 7 Drawing Sheets

OTHER PUBLICATIONS

Figure 1:
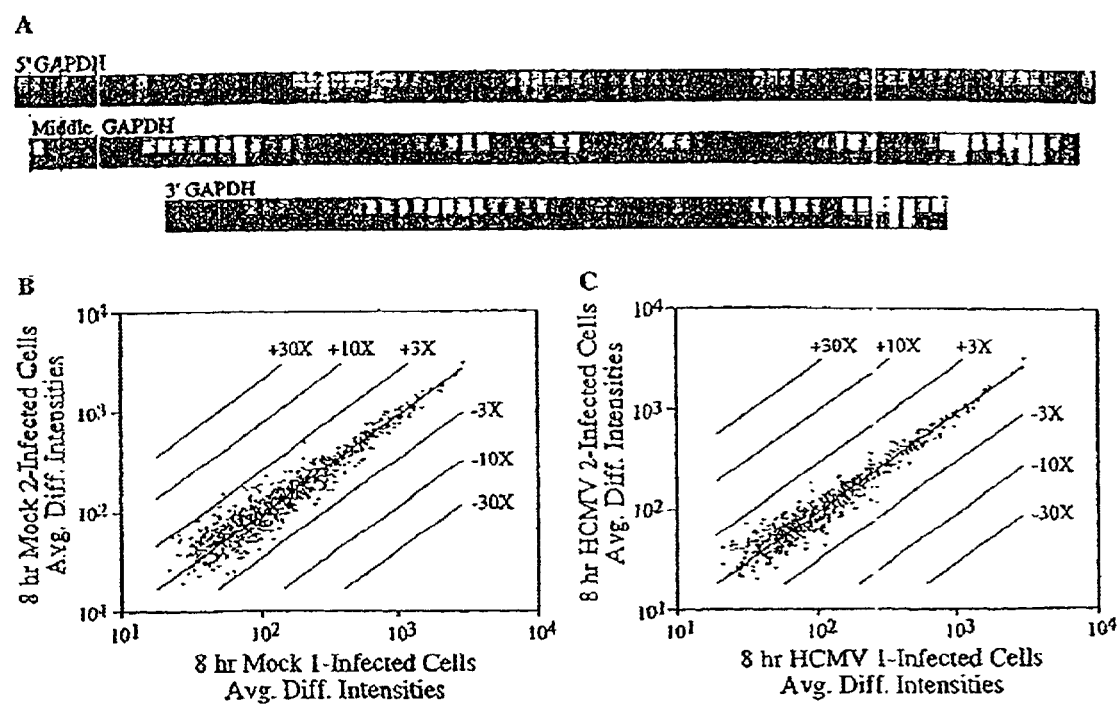

Smith D, "Microbial pathogen genomes—new strategies for identifying therapeutics and vaccine targets", Trends in Biotechnology, vol. 14, 1996, pp. 290–293.

Shiue L, "Identification of candidate genes for drug discovery by differential display", Drug Development Research, vol. 41, Jul.–Aug. 1997, pp. 142–159.

Maier E et al, "Automated array technologies for gene expression profiling", Drug Discovery Today, vol. 2, No. 8, Aug. 1997, pp. 315–324.

Bertelsen AH et al, "High–throughput gene expression analysis using SAGE", Drug Discovery Today, vol. 3, No. 4, Apr. 1996, pp. 152–159.

* cited by examiner

FIG. 4A

| | Actin/Tubulin/Myosin | | | |
|---|---|---|---|---|
| X06956 | alpha-tubulin | 24h, 6X | U | 3 |
| R59199 | est = X79535 - beta tubulin | 24h, 4X | U | 3 |
| Z24727 | tropomyosin isoform | 24h, 4X | D | 3 |
| T92451 | est = M12125 - tropomyosin | 24h, 5X | D | 3 |
| X05276 | fibroblast tropomyosin TM30 (pl) | 24h, 4X | D | 3 |
| T60155 | est = J05192 - alpha-actin (ACTA) | 24h, 11X | D | 3 |
| M19283 | gamma-actin | 24h, 4X | D | 3 |
| X54163 | cardiac troponin I | 24h, 5X | D | 3 |
| H44011 | myosin heavy chain | 8h, 5X | D | 3 |
| T55741 | est = X85337 - myosin light chain kinase (MLCK) | 24h, 6X | D | 3 |
| X53416 | actin-binding protein (filamin) (ABP-280) | 24h, 5X | D | 1 |
| T97948 | neutral calponin | 24h, 15X | D | 3 |
| | Cell Cycle | | | |
| L49231 | retinoblastoma susceptibility protein (RB1) | 24h, 12X | U | 3 |
| X59798 | PRAD1 mRNA for cyclin | 24h, 9X | D | 3 |
| D13891 | Id-2H | 8h,24h, 6-7X | D | 3 |
| L13698 | gas-1 (growth-arrest-specific gene) | 8h,24, 6-15X | D | 1 |
| X62048 | Wee1 hu | 8h,24h, 4-5X | D | 3 |
| H50438 | est = M81934 - cdc25B | 8h, 4X | D | 3 |
| U09477 | 53BP1 p53-binding protein | 8h, 5X | D | 3 |
| | Coagulation | | | |
| R16659 | est = L27624 and AC002076 - TFPI-2 | 24h, 8X | U | 1 |
| M59499 | lipoprotein-associated coagulation inhibitor | 8h, 6X | D | 3 |
| M14083 | beta-migrating plasminogen activator inhibitor 1 | 24h, 4X | D | 3 |
| J02933 | blood coagulation factor VII gene | 24h, 5X | D | 3 |
| | Complement | | | |
| M31516 | decay-accelerating factor (DAF) | 8,24h, 4-5X | U | 1 |
| T54547 | est = M84526 - adipsin/complement factor D | 24h, 7X | D | 3 |
| T69603 | est = M14058 - complement c1r component | 24h, 4X | D | 3 |
| R12676 | est = M65292 - 1.4-kb mRNA of complement factor H | 40', 4X | D | 3 |
| | Cytokines/Receptors | | | |
| M21121 | rantes | 8h, 6X | U | 2 |
| M29150 | interleukin 6 | 8h, 10X | U | 3 |
| X58377 | interleukin-11 (IL-11) | 8,24h, 4-11X | U | 1 |
| M29696 | interleukin-7 (IL-7) receptor, alpha chain | 24h, 4X | U | 1 |
| U02020 | pre-B cell enhancing factor (PBEF) | 8h,24h, 4X | U | 3 |
| T61446 | A20 | 8h, 4X | U | 3 |
| L35263 | CSaids binding protein (CSBP1) | 8h, 7X | D | 3 |
| M58286 | tumor necrosis factor receptor | 8h,24h, 4-5X | D | 1 |
| H14506 | est = L36034 - pre-B cell stimulating factor | 24h, 4X | D | 1 |
| X72012 | endoglin | 8h, 23X | D | 3 |
| | Extracellular Matrix and Cell Adhesion | | | |
| L36531 | integrin alpha 8 subunit | 40', 6X | U | 3 |
| M80244 | E16, an integral membrane protein | 40', 4X | U | 3 |
| X14787 | thrombospondin 1 (TSP1) | 24h, 21X | D | 1 |
| L12350 | thrombospondin 2 (TSP2) | 24h, 13X | D | 3 |
| X05231 | collagenase | 40',8h, 4-7X | D | 3 |
| L25285 | collagen alpha-1 type XV (COL15A1) | 24h, 13X | D | 3 |
| J03464 | collagen alpha-2 type I | 24h, 14X | D | 3 |
| M11718 | collagen alpha-2 type V | 24h, 8X | D | 3 |
| M34570 | collagen alpha-2 type VI | 24h, 6X | D | 3 |
| T51558 | est = K01228 - procollagen alpha 1(I) chain | 24h, 6X | D | 3 |
| X06700 | pro-alpha1(III) collagen | 24h, 16X | D | 1 |
| L16895 | lysyl oxidase, an extracellular copper enzyme | 24h, 4X | D | 3 |
| X53743 | fibulin-1 C - a secreted glycoprotein | 40',8,24h,5-7X | D | 3 |
| U34976 | gamma-sarcoglycan, a dystrophin-associated protein | 24h, 6X | D | 3 |
| U14394 | Tissue Inhibitor of metalloproteinases-3 (TIMP3) | 24h, 6-8X | D | 3 |
| R32771 | est = U37791 - rasi-1 matrix metalloproteinase | 8h,24h, 5-9X | D | 3 |
| U03877 | extracellular protein (S1-5) | 24h, 4X | D | 3 |
| L34056 | cadherin-11 | 24h, 9X | D | 3 |
| | GTP Binding Proteins | | | |
| H67367 | est = D38076 - RanBP1 (Ran-binding protein 1) | 24h, 5X | U | 3 |
| T93295 | est:homo. of L20294-mouse GTP-binding protein | 24h, 4X | U | 3 |
| X75593 | rab 13 | 24h, 9X | D | 3 |
| R53966 | est = Z22641 - a2-chimaerin | 24h, 8X | D | 3 |
| H19201 | est: homo. to mouse L07924 - gua. nucl. disso. stim. | 8h, 9X | D | 3 |
| | Heat Shock and Stress-Inducible Proteins | | | |
| R08183 | est = X75821, U07550 - chaperonin 10 | 24h, 8X | U | 3 |
| T66307 | heat shock 70kDa protein 1 | 24h, 11X | U | 3 |
| M86752 | transformation-sensitive protein | 24h, 8X | U | 3 |
| L08069 | heat shock protein, E. coli DnaJ homologue | 8h, 4X | U | 3 |
| H55758 | est = M14328 alpha enolase | 24h, 15X | U | 3 |
| T93272 | est = M62829 early growth response protein 1 | 8,24h, 5-6X | U | 1 |
| T51856 | est: homo. to stress-inducible chaperone mt-GrpE#1 | 24h, 4X | U | 3 |
| X79066 | ERF-1 | 8h, 4X | D | 3 |

FIG. 4B

| | | | | |
|---|---|---|---|---|
| M22349 | neuron-specific gamma-2 enolase | 24h, 6X | U | 3 |
| M24470 | glucose-6-phosphate dehydrogenase | 8h,24h, 4-14X | U | 3 |
| T47964 | purine nucleoside phosphorylase | 24h, 8X | U | 1 |
| U07681 | NAD(H)-specific isocitrate dehydrogenase α subunit | 24h, 9X | U | 3 |
| R42235 | est = X56452 - CYP2C gene for cytochrome P450 | 24h, 6X | U | 1 |
| H53120 | est = D12676 - lysosomal sialoglycoprotein | 24h, 4X | U | 3 |
| J00123 | enkephalin gene | 24h, 8X | U | 3 |
| H28131 | est = M64784 - platelet 6-phosphofructokinase | 24h, 20X | U | 3 |
| R42244 | est = X57522 - antigen peptide transporter 1 | 24h, 6X | U | 3 |
| R26294 | est = AF017732 - chromosome 2 cosmids | 24h, 4X | U | 3 |
| L25270 | XE169 | 24h, 4X | U | 3 |
| U01833 | a putative nucleotide-binding protein | 24h, 7X | U | 1 |
| H72850 | est = X56351 5 - aminolevulinate synthase | 8h,24h, 4X | U | 3 |
| U29195 | neuronal pentraxin II (NPTX2) | 24h, 7X | U | 3 |
| U19523 | GTP cyclohydrolase I | 8h,24h, 4X | U | 1 |
| H03980 | est = AB001106 - glia maturation factor | 24h, 5X | U | 3 |
| L19779 | histone H2A.2 | 8h,24h, 6-7X | U | 3 |
| Z29678 | mitF | 24h, 4-8X | D | 3 |
| X69978 | ERCC5 excision repair protein | 8h, 5X | D | 3 |
| X65024 | xeroderma pigmentosum group C compl. factor | 24h, 4X | D | 3 |
| R60318 | est = AF022813 - tetraspan (NAG-2) | 24h, 28X | D | 3 |
| H87106 | est = AF043906 - T245 protein (T245) | 24h, 4X | D | 3 |
| U14650 | platelet-endothelial tetraspan antigen 3 | 24h, 23X | D | 3 |
| L13385 | Miller-Dieker lissencephaly protein (LIS1) | 24h, 4X | D | 3 |
| L35263 | CSaids binding protein (CSBP1) | 8h, 7X | D | 3 |
| D10522 | 80K-L protein - a major substrate for protein kinase C | 8h,24h, 4-8X | D | 1 |
| J02814 | chondroitin sulfate proteoglycan core protein | 24h, 6X | D | 3 |
| X75090 | HLA-DR associated protein I (PHAPI) | 8h, 4-8X | D | 3 |
| U08092 | histamine N-methyltransferase (HNMT) | 8h, 4X | D | 3 |
| D14874 | adrenomedullin | 8h,24h, 14-18X | D | 1 |
| H80262 | est = X15422 - mannose-binding protein C | 24h, 8X | D | 3 |
| R88575 | est = U55017 M86521 - transketolase (TKT) | 24h, 5X | D | 1 |
| M13994 | cytosolic aldehyde dehydrogenase (ALDH1) | 24h, 5-7X | D | 1 |
| M22324 | aminopeptidase N/CD13 mRNA | 24h, 4X | D | 3 |
| M12996 | glucose-6-phosphate dehydrogenase (G6PD) | 24h, 5X | D | 1 |
| T52343 | est = Y00433 - glutathione peroxidase | 24h, 4X | D | 3 |
| T64167 | est = dihydrodiol dehydrogenase isozyme DD2 | 8h,24h, 4-21X | D | 3 |
| X58022 | corticotropin-releasing factor binding protein | 24h, 4X | D | 3 |
| U03688 | dioxin-inducible cytochrome P450 (CYP1B1) | 8h,24h, 4-11X | D | 3 |
| H67764 | est = U55764 - estrogen sulfotransferase | 24h, 5-12X | D | 3 |
| D00137 | class I alcohol dehydrogenase beta-1 subunit | 8h, 5X | D | 3 |
| M77836 | pyrroline 5-carboxylate reductase (EC 1.5.1.2) | 24, 15X | D | 3 |
| T57002 | est = M29038 - stem cell protein (SCL) | 24h, 4X | D | 3 |
| D13665 | est = D13665 - osteoblast specific factor 2 (OSF-2p1) | 24h, 7X | D | 3 |
| M22490 | bone morphogenetic protein-2B (BMP-2B) | 8h, 4X | D | 3 |
| M95787 | 22kDa smooth muscle protein (SM22) | 24h, 5X | D | 3 |
| Z11559 | iron regulatory factor (IRF) | 8h,24h, 5X | D | 3 |
| T63612 | ferritin heavy chain | 8h, 4X | D | 3 |
| T72863 | est = M10119 - ferritin light subunit | 24h, 287X | D | 3 |
| R56881 | est = U61166 - Xenopus laevis intersectin homolog | 8h, 4-5X | D | 3 |
| T63052 | est: homolog of M. musculusX52102 | 24h, 5X | U | 3 |
| D14663 | KIAA0107 gene | 24h, 4X | U | 3 |
| R61352 | est = D42085 KIAA0095 gene | 24h, 6X | U | 3 |
| U16954 | AF1q | 24h, 5-7X | U | 3 |
| R98335 | est = L13744 AF-9 (unknown function) | 8h, 4-5X | U | 3 |
| R01072 | est: unknown | 24h, 5X | U | 3 |
| R10664 | est: unknown | 24h, 5-7X | U | 3 |
| H24245 | est: unknown | 24h, 4-5X | U | 3 |
| H11036 | est: unknown | 24h, 6X | U | 3 |
| R42152 | est: unknown | 24h, 7X | U | 3 |
| R74454 | est: unknown | 8h,24h, 4X | U | 3 |
| R54359 | est: unknown | 24h, 10X | U | 1 |
| R01124 | est: unknown | 24h, 15X | U | 3 |
| R56443 | est: unknown | 24h, 7X | U | 3 |
| T70251 | est: unknown | 40',8h, 4X | D | 3 |
| H92205 | est: unknown | 8h, 4X | D | 3 |
| T89666 | est: unknown | 8h, 4X | D | 3 |
| H13281 | est: unknown | 24h, 15X | D | 3 |
| R60741 | est: unknown | 8h, 4X | D | 3 |
| H16597 | est: unknown | 24h, 4X | D | 3 |
| R40403 | est: unknown | 24h, 6X | D | 3 |
| H78404 | est: unknown | 8h, 4X | D | 3 |
| T48692 | est: unknown | 8h,24h, 6X | D | 1 |
| H40677 | est: unknown | 8h, 6X | D | 3 |
| H86071 | est: homology to mouse AF003234 | 8h, 5X | D | 3 |

FIG. 4C

| Accession | Description | Time, Fold | U/D | Cluster |
|---|---|---|---|---|
| Interferon | | | | |
| M24594 | interferon stimulated genes 54K (isg54K) | 8h,24h, 5-19X | U | 2 |
| M87434 | 71 kDa 2'5' oligoadenylate synthetase | 8h, 6X | U | 2 |
| X02875 | (2'-5') oligo A synthetase E (1.8 kb RNA) | 8h,24h, 6-15X | U | 2 |
| X02874 | (2'-5') oligo A synthetase E (1.6 kb RNA) | 8h, 8X | U | 2 |
| M87284 | 69 kDa 2'5' oligoadenylate synthetase | 8h, 8X | U | 2 |
| X02530 | gamma-interferon inducible early response gene | 8h,h, 34X | U | 1 |
| L05072 | interferon regulatory factor 1 (IRF-1) | 24h, 7X | U | 2 |
| X15949 | interferon regulatory factor-2 (IRF-2) | 8h, 5-12X | U | 2 |
| X67325 | interferon-alpha inducible gene; p27 gene | 24h, 7-28X | U | 2 |
| H05300 | interferon-induced guanylate-binding protein 1 | 8h,24h, 9-27X | U | 2 |
| M55542 | guanylate binding protein isoform II | 8h, 9X | U | 2 |
| D31887 | KIAA0062 (cig19) | 8h,24h, 3-4X | U | 2 |
| X82200 | interferon inducible gene staf50 | 24h, 14X | U | 1 |
| X02492 | interferon-induced protein 6-16 | 8h,24h, 4-5X | U | 2 |
| R34698 | interferon-inducible protein 9-27 | 8h,24h, 3-6X | U | 2 |
| M13755 | interferon-induced 17-kDa/15-kDa protein | 8,24h, 55-260X | U | 2 |
| M28622 | interferon beta | 8h,24h, 10-31X | U | 2 |
| X17668 | indoleamine 2,3-dioxygenase | 8h,24h, 9-140X | U | 1 |
| M33882 | MxA | 8h,24h, 5-118X | U | 2 |
| M30818 | MxB | 8h,24h, 23-53X | U | 2 |
| X56841 | HLA-E gene | 8h,24h, 5-19X | U | 1 |
| T50250 | est: homo. to U51904, mouse IFN α-treated mRNA | 24h, 32X | U | 1 |
| M60618 | nuclear autoantigen Sp100 | 8h,24h, 4-16X | U | 2 |
| M73778 | PML-1 | 8h,24h, 3-6X | U | 2 |
| Kinase/Phosphatase | | | | |
| R39857 | est = X97630 - serine/threonine protein kinase EMK | 24h, 4X | U | 3 |
| H02889 | est = Y11366 IMPA gene | 24h, 8X | U | 3 |
| U25994 | cell death protein (RIP protein kinase) | 8h, 4X | U | 1 |
| D21209 | protein tyrosine phosphatase (PTP-BAS, type 1) | 8h,24h, 4-6X | D | 1 |
| X77278 | HYL tyrosine kinase | 24h, 8X | D | 3 |
| R60908 | est = X74764 - receptor protein tyrosine kinase | 24h, 21X | D | 1 |
| H65441 | est = U78027, L35265 - Bruton's tyrosine kinase | 24h, 7X | D | 3 |
| X16416 | proto-oncogene tyrosine-protein kinase (abl) | 24h, 4X | D | 1 |
| Lamins | | | | |
| M55210 | laminin B2 chain | 24h, 4-8X | D | 3 |
| X79683 | bata2 laminin | 24h, 4-5X | D | 3 |
| R43734 | S78569 - laminin alpha 4 chain | 24h, 6X | D | 3 |
| T55218 | est = M13452 or M13451 - lamin A or C | 8h, 26X | D | 3 |
| Ligands and Receptors | | | | |
| L13740 | TR3 orphan receptor | 8,24h,6-46X | U | 1 |
| U12767 | mitogen induced nuclear orphan receptor | 8h, 5X | U | 3 |
| M77140 | pro-galanin | 24h, 20X | U | 1 |
| M63888 | heparin-binding growth factor receptor | 24h, 9X | U | 3 |
| T70920 | est = M88279 - immunophilin (FKBP52) | 24h, 8X | U | 3 |
| M20132 | androgen receptor (AR) | 8h, 4X | D | 3 |
| M19481 | follistatin | 24h, 6-15X | D | 1 |
| T71662 | est = M14118 - insulin-like growth factor (IGF-II) | 24h, 4X | D | 1 |
| M35878 | insulin-like growth factor-binding protein-3 | 24h, 4X | D | 3 |
| M65062 | insulin-like growth factor-binding protein-5 | 8h,24h, 4-12X | D | 3 |
| M35410 | insulin-like growth factor binding protein 2 | 40',8h, 5-11X | D | 3 |
| X04434 | insulin-like growth factor 1 receptor | 40',8h,24h, 4X | D | 3 |
| L07594 | transforming growth factor-beta type III receptor | 8h,24h, 4-6X | D | 1 |
| M21574 | platelet-derived growth factor receptor alpha | 8h,24h, 12-25X | D | 1 |
| H88938 | est = M60828 M25295 - keratinocyte growth factor | 8h, 4X | D | 3 |
| X62381 | activin receptor; growth factor-like receptor | 8h, 6X | D | 3 |
| R45296 | est = U67784 - orphan G protein-coupled receptor | 24h, 6X | D | 3 |
| X02157 | fetal erythropoietin | 24h, 4X | D | 3 |
| M64497 | apolipoprotein AI regulatory protein (ARP-1) | 8h, 4-5X | D | 1 |
| L11708 | 17 beta hydroxysteroid dehydrogenase type 2 | 24h, 7X | D | 3 |
| L00352 | low density lipoprotein (LDL) receptor | 8h,24h, 5-6X | D | 3 |
| M10065 | apolipoprotein E | 40',8h, 7-26X | D | 3 |
| Prostaglandin Synthesis | | | | |
| U04636 | cyclooxygenase-2 (cox2) | 8h, 7X | U | 2 |
| M72393 | cytosolic phospholipase A2 (cPLA2) | 8h,24h, 7-12X | U | 3 |
| X05908 | lipocortin | 24h, 9X | D | 3 |
| D38145 | prostacyclin synthase | 24h, 4X | D | 3 |
| Protein Degradation | | | | |
| T56244 | est = D26599 - proteasome subunit HsC7-I | 24h, 6X | U | 3 |
| T54276 | proteasome subunit LMP7 (allele LMP7C) | 8h, 4X | U | 3 |
| T92259 | proteasome component IOTA chain | 24h, 5X | U | 3 |
| D00762 | proteasome component HC8 | 24h, 6X | U | 3 |
| D00760 | proteasome component C3 | 24h, 5X | U | 3 |
| H05893 | 26S proteasome subunit p97 | 24h, 4X | U | 3 |
| L02426 | 26S protease (S4) regulatory subunit | 24h, 16X | U | 3 |
| M91670 | ubiquitin carrier protein (E2-EPF) | 24h, 4X | U | 1 |
| R67921 | est = D55696 - putative cysteine protease | 8h, 4X | U | 3 |
| T56256 | est = U20657 - ubiquitin protease proto-oncogene | 8h, 4X | D | 3 |
| J03589 | ubiquitin-like protein (GdX) | 24h, 7X | D | 3 |
| T50500 | est = Z22658 - a placental thrombin inhibitor (PTI) | 24h, 4X | D | 3 |

FIG. 4D

| | Proto-oncogenes | | | |
|---|---|---|---|---|
| X89985 | BCL7B gene | 8h,24h, 5-10X | U | 1 |
| H48122 | est = U43746, breast cancer susceptibility (BRCA2) | 8h, 4X | U | 1 |
| M83751 | arginine-rich protein (ARP) | 24h, 11X | U | 3 |
| M27903 | pim-1 proto-oncogene | 24h, 16X | U | 3 |
| T53138 | est = Y11306 - hTCF-4 | 8h, 4X | U | 3 |
| X16416 | proto-oncogene tyrosine-protein kinase (abl) | 24h, 4X | D | 1 |
| D43969 | AML1c protein | 8h,24h, 4X | D | 3 |
| X82209 | MN1 | 8h,24h, 4-7X | D | 3 |
| Splicing Factors | | | | |
| X13482 | U2 small nuclear ribonucleoprotein A' | 24h, 4X | U | 3 |
| M15841 | U2 small nuclear RNA-associated B" | 24h, 4X | U | 3 |
| R41349 | splicing factor, arginine/serine-rich 7 (SFRS7) | 24h, 10X | U | 3 |
| Transcription Factors | | | | |
| R55041 | est = J03161 - serum response factor (SRF) | 24h, 5X | U | 3 |
| H46624 | est: homology to mouse AB012276 - ATFx | 8h, 4X | U | 3 |
| M97676 | homeobox protein (HOX7) | 8h, 4X | U | 1 |
| R26139 | est = X59268 - TFIIB | 8h, 8X | U | 1 |
| M69043 | MAD-3, encodes an I kappa B-like protein | 8h,24h, 6-10X | U | 1 |
| R26146 | NF-kB p105 subunit | 24h, 4X | U | 3 |
| U09825 | acid finger protein (AFP) | 8h,24h, 5-8X | U | 1 |
| H88261 | est = U90304 Iroquois-class homeodomain protein | 8h, 4X | U | 3 |
| X03348 | beta-glucocorticoid receptor | 8h,24h, 4X | D | 3 |
| M83667 | NF-IL6-beta protein | 8h,24, 4-6X | D | 1 |
| X57435 | transcription factor AP-4 | 8h,24, 4X | D | 3 |
| M36711 | sequence-specific DNA-binding protein (AP-2) | 8h, 6X | D | 3 |
| Y00345 | polyA binding protein | 24h, 5X | D | 3 |
| R39209 | est = X65644 - MBP-2 for MHC binding protein 2 | 24h, 5X | D | 3 |
| L19872 | aryl hydrocarbon receptor (AhR) | 8h,24h, 4-8X | D | 3 |
| Translation Factors | | | | |
| R72300 | est = U17969 - tranlation initiation factor eIF-5A | 24h, 149X | U | 1 |
| H04333 | est = U49436 - translation initiation factor 5 (eIF5) | 24h, 4X | U | 3 |
| T69446 | est = D13748 - initiation factor 4A-1 (eIF-4A1) | 24h, 36X | U | 3 |
| L18960 | translation initiation factor (eIF-4C) | 24h, 39X | U | 3 |
| H01943 | eukaryotic initiation factor 4E (eIF-4E) | 24h, 4X | U | 3 |
| X62570 | IFP53, trypotophanyl-tRNA synthetase | 8h,24h, 6-800X | U | 1 |
| M81592 | gamma-glutamyl carboxylase (hGC) | 24h, 5X | U | 3 |
| Z12830 | SSR (signal-sequence receptor) alpha subunit | 24h, 5X | U | 3 |
| R60357 | alanyl tRNA synthetase | 8h, 5X | D | 2 |
| D31762 | KIAA0057 gene - homolog of TRAMP | 24, 8X | D | 3 |
| Miscellaneous | | | | |
| M34551 | 52k autoantigen in Ro/SSA ribonucleoprotein compl. | 8h,24h, 4-12X | U | 3 |
| U33286 | chromosome segregation gene homolog CAS | 24h, 4X | U | 3 |
| T88721 | est = U52100, X94770 - XMP mRNA | 24h, 4X | U | 3 |
| M26697 | nucleolar phosphoprotein B23 | 24h, 12X | U | 3 |
| J05682 | subunit C of V-ATPase (vat C) | 24h, 8X | U | 1 |

EXPRESSION MONITORING FOR HUMAN CYTOMEGALOVIRUS (HCMV) INFECTION

The present application is a continuation of U.S. application Ser. No. 09/377,907, filed Aug. 20, 1999 now abandoned which claims the benefit of U.S. provisional application Ser. Number 60/097,708, filed Aug. 21, 1998.

BACKGROUND OF THE INVENTION

Many biological functions are accomplished by altering the expression of various genes through transcriptional (e.g. through control of initiation, provision of RNA precursors, RNA processing, etc.) and/or translational control. For example, fundamental biological processes such as cell cycle, cell differentiation and cell death, are often characterized by the variations in the expression levels of groups of genes.

Gene expression is also associated with pathogenesis. For example, the lack of sufficient expression of functional tumor suppressor genes and/or the over expression of oncogene/protooncogenes could lead to tumorigenesis (Marshall, Cell, 64: 313–326 (1991); Weinberg, Science, 254: 1138–1146 (1991), incorporated herein by reference for all purposes). Thus, changes in the expression levels of particular genes (e.g. oncogenes or tumor suppressors) serve as signposts for the presence and progression of various diseases.

The study of gene expression in the art has been generally concentrated on the regulatory regions of the gene of interest and on the relationships among a few genes. A number of transcriptional factors/DNA binding proteins have been identified and a limited number of regulatory pathways have been discovered. However, the expression of a particular gene is frequently regulated by the expression of a large number of other genes. The expression of those regulatory genes may also be under the control of additional genes. This complex regulatory relationship among genes constitutes a genetic network. The function and regulation of a particular gene can be best understood in the context of this genetic network. As the Human Genome Project and commercial genome research progress at a great rate, most, if not all, of the expressed genes will be partially sequenced in the near future. Understanding the functions and regulatory relationships among the large number of genes is becoming a difficult task with traditional tools. Therefore, there is a need in the art to develop a systematic approach to understand the complex regulatory relationships among large numbers of genes.

SUMMARY OF THE INVENTION

This invention provides methods, compositions, and apparatus for studying the complex regulatory relationships among host genes and viruses, in particular HCMV. In some of its specific applications, this invention provides methods, compositions, and apparatus for identifying drugs for preventing or ameliorating disease symptoms caused by HCMV. In other applications the invention provides methods for determining the stage of infection or the extent of tissue damage caused by HCMV infection. In another embodiment the invention provides a general method for narrowing large sets of genes which may be important down to smaller subsets of genes which have elevated probabilities of being biologically, physiologically, and medically relevant.

BRIEF DESCRIPTION OF THE DRAWINGS AND TABLE

FIG. 1. Characterization of RNA target samples and reproducibility of array-based hybridization results. (FIG. 1A) 82, 68 and 51 probe pairs were used to interrogate the 5', middle and 3' portions of the GAPDH mRNA, which is constitutively expressed in fibroblasts. (FIG. 1B, FIG. 1C) The plots compare the average difference intensities (Avg. Diff. Intensities) of the 20 probe pairs interrogating each of the genes present in two independent experiments performed on the mock-infected cells (FIG. 1A) or cells at 8 h after infection (FIG. 1B). The parallel lines flanking the center diagonal line indicate 3, 10 and 30-fold changes in intensity. With the exception of the thombospondin-1 gene in the mock-infected control, all other genes demonstrated an average difference in their hybridization intensities of less than 3-fold.

FIG. 2A, FIG. 2B, FIG. 2C. Global survey of the differences in mRNA levels after HCMV infection.

The plots show the variation in expression levels (Avg. Diff. Intensities) between mock-infected cells and cells at 40 min, 8 h and 24 h after infection (FIG. 2A, FIG. 2B, FIG. 2C, respectively). Changes in expression of 3, 10, and 30-fold are highlighted by the parallel lines flanking the center diagonal line.

Figure 3:
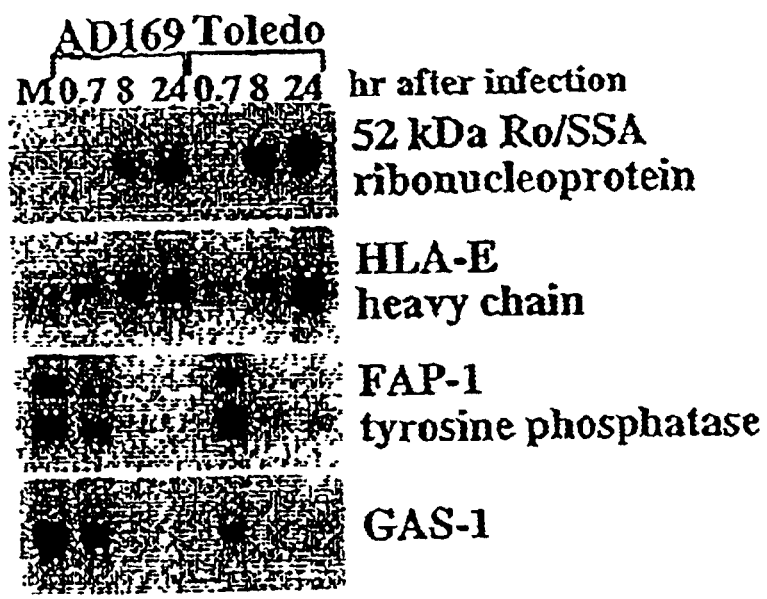

FIG. 3. Representative Northern blot analyses confirming changes in mRNA levels predicted by DNA array assay. Cultures of primary human diploid fibroblasts were infected with HCMV strain AD169 or Toledo, and total cellular RNA was analyzed by Northern blot at 40 min, 8 h and 24 h after infection. Genes to which the probes correspond are identified to the right of the autoradiograms. M, mock-infected cells.

FIGS. 4A–4D (Table 1). Cellular mRNAs whose levels change by a factor of four or more after infection with HCMV. Identity of columns from left to right: GenBank accession number; name of gene encoding mRNA; time(s) after infection when a change in mRNA level was observed plus fold change; increase (U) or decrease (D) in steady state level of RNA; gene chip results confirmed in this report by northern blot (1), confirmed by another literature report (2), not confirmed (3).

DETAILED DESCRIPTION OF THE INVENTION

I. Definitions

Bind(s) substantially: "Bind(s) substantially" refers to complementary hybridization between a probe nucleic acid and a target nucleic acid and embraces minor mismatches that can be accommodated by reducing the stringency of the hybridization media to achieve the desired detection of the target polynucleotide sequence.

Background: The terms "background" or "background signal intensity" refer to hybridization signals resulting from non-specific binding, or other interactions, between the labeled target nucleic acids and components of the oligonucleotide array (e.g., the oligonucleotide probes, control probes, the array substrate, etc.). Background signals may also be produced by intrinsic fluorescence of the array components themselves. A single background signal can be calculated for the entire array, or a different background signal may be calculated for each target nucleic acid. In a preferred embodiment, background is calculated as the average hybridization signal intensity for the lowest 5% to 10% of the probes in the array, or, where a different background signal is calculated for each target gene, for the lowest 5% to 10% of the probes for each gene. Of course, one of skill in the art will appreciate that where the probes to a particular gene hybridize well and thus appear to be specifically binding to a target sequence, they should not be used in a background signal calculation. Alternatively, background may be calculated as the average hybridization signal intensity produced by hybridization to probes that are not complementary to any sequence found in the sample (e.g. probes directed to nucleic acids of the opposite sense or to genes not found in the sample such as bacterial genes where the sample is mammalian nucleic acids). Background can also be calculated as the average signal intensity produced by regions of the array that lack any probes at all.

Cis-acting: The term "cis-acting" is used here to refer to the regulation of gene expression by a DNA subsequence in the same DNA molecule as the target gene. Cis-acting can be exerted either by the binding of trans-acting transcriptional factors or by long range control.

Complexity: The term "complexity" is used here according to standard meaning of this term as established by Britten et al. *Methods of Enzymol.* 29:363 (1974). See, also *Cantor and Schimmel Biophysical Chemistry:* Part III at 1228–1230 for further explanation of nucleic acid complexity.

Hybridizing specifically to: The phrase "hybridizing specifically to" refers to the binding, duplexing, or hybridizing of a molecule substantially to or only to a particular nucleotide sequence or sequences under stringent conditions when that sequence is present in a complex mixture (e.g., total cellular) DNA or RNA.

Introns: noncoding DNA sequences which separate neighboring coding regions. During gene transcription, introns, like exons, are transcribed into RNA but are subsequently removed by RNA splicing.

Massive Parallel Screening: The phrase "massively parallel screening" refers to the simultaneous screening of at least about 100, preferably about 1000, more preferably about 10,000 and most preferably about 1,000,000 different nucleic acid hybridizations.

Mismatch control: The term "mismatch control" or "mismatch probe" refer to a probe whose sequence is deliberately selected not to be perfectly complementary to a particular target sequence. For each mismatch (MM) control in a high-density array there typically exists a corresponding perfect match (PM) probe that is perfectly complementary to the same particular target sequence. The mismatch may comprise one or more bases. While the mismatch(es) may be located anywhere in the mismatch probe, terminal mismatches are less desirable as a terminal mismatch is less likely to prevent hybridization of the target sequence. In a particularly preferred embodiment, the mismatch is located at or near the center of the probe such that the mismatch is most likely to destabilize the duplex with the target sequence under the test hybridization conditions.

mRNA or transcript: The term "mRNA" refers to transcripts of a gene. Transcripts are RNA including, for example, mature messenger RNA ready for translation, products of various stages of transcript processing. Transcript processing may include splicing, editing and degradation.

Nucleic Acid: The terms "nucleic acid" or "nucleic acid molecule" refer to a deoxyribonucleotide or ribonucleotide polymer in either single-or double-stranded form, and unless otherwise limited, would encompass analogs of natural nucleotide that can function in a similar manner as naturally occurring nucleotide. An oligo-nucleotide is a single-stranded nucleic acid of 2 to n bases, where n may be greater than 500 to 1000. Nucleic acids may be cloned or synthesized using any technique known in the art. They may also include non-naturally occurring nucleotide analogs, such as those which are modified to improve hybridization and peptide nucleic acids.

Nucleic acid encoding a regulatory molecule: The regulatory molecule may be DNA, RNA or protein. Thus for example DNA sites which bind protein or other nucleic acid molecules are included within the class of regulatory molecules encoded by a nucleic acid.

Perfect match probe: The term "perfect match probe" refers to a probe that has a sequence that is perfectly complementary to a particular target sequence. The test probe is typically perfectly complementary to a portion (subsequence) of the target sequence. The perfect match (PM) probe can be a "test probe", a "normalization control" probe, an expression level control probe and the like. A perfect match control or perfect match probe is, however, distinguished from a "mismatch control" or "mismatch probe."

Probe: As used herein a "probe" is defined as a nucleic acid, capable of binding to a target nucleic acid of complementary sequence through one or more types of chemical bonds, usually through complementary base pairing, usually through hydrogen bond formation. As used herein, a probe may include natural (i.e. A, G, U, C, or T) or modified bases (7-deazaguanosine, inosine, etc.). In addition, the bases in probes may be joined by a linkage other than a phosphodiester bond, so long as it does not interfere with hybridization. Thus, probes may be peptide nucleic acids in which the constituent bases are joined by peptide bonds rather than phosphodiester linkages.

Target nucleic acid: The term "target nucleic acid" refers to a nucleic acid (often derived from a biological sample), to which the probe is designed to specifically hybridize. It is either the presence or absence of the target nucleic acid that is to be detected, or the amount of the target nucleic acid that is to be quantified. The target nucleic acid has a sequence that is complementary to the nucleic acid sequence of the corresponding probe directed to the target. The term target nucleic acid may refer to the specific subsequence of a larger nucleic acid to which the probe is directed or to the overall sequence (e.g., gene or mRNA) whose expression level it is desired to detect. The difference in usage will be apparent from context.

Trans-acting: The term "trans-acting" refers to regulation of gene expression by a product that is encoded by a gene at a remote location, usually as a result of binding to a cis-element.

Stringent conditions The term "stringent conditions" refers to conditions under which a probe will hybridize to its target subsequence, but with only insubstantial hybridization to other sequences or to other sequences such that the difference may be identified. Stringent conditions are sequence-dependent and will be different in different circumstances. Longer sequences hybridize specifically at higher temperatures. Generally, stringent conditions are selected to be about 5° C. lower than the thermal melting point (Tm) for the specific sequence at a defined ionic strength and pH.

Subsequence: "Subsequence" refers to a sequence of nucleic acids that comprise a part of a longer sequence of nucleic acids.

Thermal melting point (Tm): The Tm is the temperature, under defined ionic strength, pH, and nucleic acid concentration, at which 50% of the probes complementary to the target sequence hybridize to the target sequence at equilibrium. As the target sequences are generally present in excess, at Tm, 50% of the probes are occupied at equilibrium). Typically, stringent conditions will be those in which the salt concentration is at least about 0.01 to 1.0 M Na ion concentration (or other salts) at pH 7.0 to 8.3 and the temperature is at least about 30 C. for short probes (e.g., 10 to 50 nucleotide). Stringent conditions may also be achieved with the addition of destabilizing agents such as formamide.

Quantifying: The term "quantifying" when used in the context of quantifying transcription levels of a gene can refer to absolute or to relative quantification. Absolute quantification may be accomplished by inclusion of known concentration(s) of one or more target nucleic acids (e.g. control nucleic acids such as Bio B or with known amounts the target nucleic acids themselves) and referencing the hybridization intensity of unknowns with the known target nucleic acids (e.g. through generation of a standard curve). Alternatively, relative quantification can be accomplished by comparison of hybridization signals between two or more genes, or between two or more treatments to quantify the changes in hybridization intensity and, by implication, transcription level.

Sequence identity: The "percentage of sequence identity" or "sequence identity" is determined by comparing two optimally aligned sequences or subsequences over a comparison window or span, wherein the portion of the polynucleotide sequence in the comparison window may optionally comprise additions or deletions (i.e., gaps) as compared to the reference sequence (which does not comprise additions or deletions) for optimal alignment of the two sequences. The percentage is calculated by determining the number of positions at which the identical subunit (e.g. nucleic acid base or amino acid residue) occurs in both sequences to yield the number of matched positions, dividing the number of matched positions by the total number of positions in the window of comparison and multiplying the result by 100 to yield the percentage of sequence identity. Percentage sequence identity when calculated using the programs GAP or BESTFIT (see below) is calculated using default gap weights.

Methods of alignment of sequences for comparison are well known in the art. Optimal alignment of sequences for comparison may be conducted by the local homology algorithm of Smith and Waterman, *Adv. Appl. Math.* 2: 482 (1981), by the homology alignment algorithm of Needleman and Wunsch *J. Mol. Biol.* 48: 443 (1970), by the search for similarity method of Pearson and Lipman, *Proc. Natl. Acad. Sci. USA* 85: 2444 (1988), by computerized implementations of these algorithms (including, but not limited to CLUSTAL in the PC/Gene program by Intelligenetics, Moutain View, Calif., GAP, BESTFIT, FASTA, and TFASTA in the Wisconsin Genetics Software Package, Genetics Computer Group (GCG), 575 Science Dr., Madison, Wis., USA), or by inspection. In particular, methods for aligning sequences using the CLUSTAL program are well described by Higgins and Sharp in *Gene,* 73: 237–244 (1988) and in *CABIOS* 5: 151–153 (1989)).

Up-stream or down-stream gene. If the expression of a first gene is regulated by a second gene, the second gene is called an "up-stream gene" for the first gene and the first gene is the "down-stream" gene of the second gene. The regulation of the first gene by second gene could be through transactivation. For example, the first gene encodes a transcriptional factor that controls the expression of the second gene. The regulation can also be exerted by cis-acting. For example, the first gene is in the proximity of the second gene and exerts a positional effect on the expression of the second gene. In this case, the first gene does not have to be expressed in order to have an influence on the second gene.

According to the present invention, the stage of disease caused by HCMV infection can be determined. Expression levels of one or more genes which are induced or repressed by HCMV are determined in a first human cell sample. The first human cell sample comprises cells of a patient infected with HCMV and consists essentially of HCMV-infected cells. The expression levels of the one or more genes correlates with stage of disease progression of the HCMV infection.

According to another embodiment of the invention the extent of tissue damage caused by HCMV infection is determined. Expression levels of one or more genes which are induced or repressed by HCMV are determined in a first human cell sample. The first human cell sample comprises cells of a patient infected with HCMV and consists essentially of HCMV-infected cells. The expression levels of the one or more genes correlates with extent of tissue damage caused by the HCMV infection.

According to yet another aspect of the invention candidate drugs for preventing or ameliorating disease symptoms caused by HCMV are identified. Human cells are contacted with HCMV and a test agent. The contacting of the test agent and the HCMV with the cells can be at the same time or sequentially. Expression levels of one or more genes which are induced or repressed by HCMV are determined. Test agents are identified as candidate drugs if the test agents cause the human cells to express the one or more genes at the same (i.e., within 10–50% ) of the level at which the human cells express the one or more genes in the absence of HCMV infection.

The genes whose expression levels are tested are those which are induced or repressed by HCMV. These are preferably those which are induced or repressed to a level which is at least two-fold, four-fold, eight-fold, ten-fold, fifteen-fold different than the level of expression in the absence of HCMV. More preferably the genes are selected from those genes identified in Table 1 as repressed or induced by HCMV. Of those genes which are identified in Table 1, HLA-E, Ro/SSA, lipocortin-1, cPLA2, COX-2, thrombospondin-1, and MITF, are preferred.

According to another aspect of the invention a general paradigm for identifying subsets of biologically, physiologically, or medically relevant genes is provided. This paradigm permits the prioritization of attention, investigation, and research on those genes which are most likely to have biologically, physiologically, or medically relevance. The paradigm involves the combination of expression data with other types of information contained within databases, including the general scientific literature, the patent literature, nucleotide and amino acid sequence databases, etc. By systematically searching databases for information which may shed light on the source of the expression data, one can make new connections and correlations which will confirm or suggest heightened biological, physiological, or medical relevance. The discussion section of the Example provides multiple examples of the operation of this paradigm. Generally, expression levels of at least two genes are compared between two cell samples. The two cell samples are the same but for a selected environmental, genetic, or developmental difference. These include without limitation contact with a drug or other exogenous chemical agent; temperature difference; mutation; viral infection; developmental stage difference; and bacterial infection. A set of genes whose expression levels differ between the two cell samples is identified. A database is searched to identify an environmental agent, gene, disease, biological phenomenon, or developmental stage previously associated with expression or loss of expression of individual members of the set of genes. As exemplified below, these may include without limitation an immunological reaction, a biochemical pathway, knock-out experimental animals, mutant animals or cells, diseases. When a common biological feature is identified between the selected environmental, genetic, or developmental difference used between the two sets of cells and the unselected environmental agent, gene, disease, or developmental stage identified from the database, the common gene is identified as being a member of a subset of genes which are improved targets for drug development. A common biological feature may be, for example, an association with a symptom of a disease, a phenotype, a reaction, etc. A computer-readable medium having computer-executable instructions may also be used for performing the steps of this paradigm. Such a medium may be stored on disk or other suitable medium, as is well known in the art.

The method by which expression levels are determined is not critical to the invention. Either mRNA or protein expression from one or more genes may be determined. Any method known the art for determining such expression levels can be used. These include without limitation hybridization to an array of oligonucleotides, serial analysis of gene expression, hybridization on a solid support, and immunological assays, such as Western blot, ELISA, immunohistochemistry. mRNA can be collected from the human cells, reverse transcribed, and used as a template for amplification. Any detection means known in the art can be used, including but not limited to use of a radioactive label, a fluorescent label, a chromophoric label, an enzymatic label.

Various techniques known in the art render the screening of large numbers of genes' expression relatively straightforward. Thus although a single gene's expression can be determined and can provide diagnostic and prognostic information, multiple genes can also be tested for their expression levels. In some embodiments at least 2, 5, 10, 15, 25, 50, 100, 150, 200, 350, 500, or 1000 genes are tested to determine their expression levels.

Cell samples for use in the assays of the present invention can be any cell type which is infected by HCMV. These include but are not limited to human cells fibroblasts, lymphocytes, epithelial cells, lung epithelial cells, and neuronal cells. When comparisons are done between an HCMV-infected cell sample and an uninfected cell sample, preferably the two samples are of the cell type. However this is not always possible. Comparisons can also be done with consensus expression profiles determined using a population of cells from normal, uninfected cells.

Once expression levels of one or more genes are determined in a clinical human cell sample from HCMV-infected cells, they can be compared to the level found in uninfected controls, whether from the same individual and preferably the same type of cell, or from other individuals. A level of induction or repression greater than the predetermined threshold can be correlated with a stage of disease progression or extent of tissue damage. Such correlation can be made by reference to a standard curve generated of stage of disease progression or extent of tissue damage as a function of gene expression levels.

The methods of the invention involve quantifying the level of expression of a large number of genes. In some preferred embodiments, a high density oligonucleotide array is used to hybridize with a target nucleic acid sample to detect the expression level of a large number of genes, preferably more than 10, more preferably more than 100, and most preferably more than 1000 genes.

Activity of a gene is reflected by the activity of its product(s): the proteins or other molecules encoded by the gene. Those product molecules perform biological functions. Directly measuring the activity of a gene product is, however, often difficult for certain genes. Instead, the immunological activities or the amount of the final product(s) or its peptide processing intermediates are determined as a measurement of the gene activity. More frequently, the amount or activity of intermediates, such as transcripts, RNA processing intermediates, or mature mRNAs are detected as a measurement of gene activity.

In many cases, the form and function of the final product(s) of a gene is unknown. In those cases, the activity of a gene is measured conveniently by the amount or activity of transcript(s), RNA processing intermediate(s), mature mRNA(s) or its protein product(s) or functional activity of its protein product(s).

Any methods that measure the activity of a gene are useful for at least some embodiments of this invention. For example, traditional Northern blotting and hybridization, nuclease protection, RT-PCR and differential display have been used for detecting gene activity. Those methods are useful for some embodiments of the invention. However, this invention is most useful in conjunction with methods for detecting the expression of a large number of genes.

High density arrays are particularly useful for monitoring the expression control at the transcriptional, RNA processing and degradation level. The fabrication and application of high density arrays in gene expression monitoring have been disclosed previously in, for example, WO 97/10365, WO 92/10588, U.S. application Ser. No. 08/772,376 filed Dec. 23, 1996; Ser. No. 08/529,115 filed on Sep. 15, 1995; Ser. No. 08/168,904 filed Dec. 15, 1993; Ser. No. 07/624,114 filed on Dec. 6, 1990, Ser. No. 07/362,901 filed Jun. 7, 1990, all incorporated herein for all purposed by reference. In some embodiment using high density arrays, high density oligonucleotide arrays are synthesized using methods such as the Very Large Scale Immobilized Polymer Synthesis (VLSIPS) disclosed in U.S. Pat. No. 5,445,934 in corporated herein for all purposes by reference. Each oligonucleotide occupies a known location on a substrate. A nucleic acid target sample is hybridized with a high density array of oligonucleotides and then the amount of target nucleic acids hybridized to each probe in the array is quantified. One preferred quantifying method is to use confocal microscope and fluorescent labels. The GeneChip® system (Affymetrix, Santa Clara, Calif.) is particularly suitable for quantifying the hybridization; however, it will be apparent to those of skill in the art that any similar systems or other effectively equivalent detection methods can also be used.

High density arrays are suitable for quantifying a small variations in expression levels of a gene in the presence of a large population of heterogeneous nucleic acids. Such high density arrays can be fabricated either by de novo synthesis on a substrate or by spotting or transporting nucleic acid sequences onto specific locations of substrate. Nucleic acids are purified and/or isolated from biological materials, such as a bacterial plasmid containing a cloned segment of sequence of interest. Suitable nucleic acids are also produced by amplification of templates. As a nonlimiting illustration, polymerase chain reaction, and/or in vitro transcription, are suitable nucleic acid amplification methods.

Synthesized oligonucleotide arrays are particularly preferred for this invention. Oligonucleotide arrays have numerous advantages, as opposed to other methods, such as efficiency of production, reduced intra- and inter array variability, increased information content and high signal-to-noise ratio.

Preferred high density arrays for gene function identification and genetic network mapping comprise greater than about 100, preferably greater than about 1000, more preferably greater than about 16,000 and most preferably greater than 65,000 or 250,000 or even greater than about 1,000,000 different oligonucleotide probes, preferably in less than 1 $cm^2$ of surface area. The oligonucleotide probes range from about 5 to about 50 or about 500 nucleotides, more preferably from about 10 to about 40 nucleotide and most preferably from about 15 to about 40 nucleotides in length.

Massive Parallel Gene Expression Monitoring

One preferred method for massive parallel gene expression monitoring is based upon high density nucleic acid arrays. Nucleic acid array methods for monitoring gene expression are disclosed and discussed in detail in PCT Application WO 092.10588 published on Jun. 25, 1992), all incorporated herein by reference for all purposes.

Generally those methods of monitoring gene expression involve (a) providing a pool of target nucleic acids comprising RNA transcript(s) of one or more target gene(s), or nucleic acids derived from the RNA transcript(s); (b) hybridizing the nucleic acid sample to a high density array of probes and (c) detecting the hybridized nucleic acids and calculating a relative and/or absolute expression (transcription, RNA processing or degradation) level.

(A) Providing a Nucleic Acid Sample

One of skill in the art will appreciate that it is desirable to have nucleic samples containing target nucleic acid sequences that reflect the transcripts of interest. Therefore, suitable nucleic acid samples may contain transcripts of interest. Suitable nucleic acid samples, however, may contain nucleic acids derived from the transcripts of interest. As used herein, a nucleic acid derived from a transcript refers to a nucleic acid for whose synthesis the mRNA transcript or a subsequence thereof has ultimately served as a template. Thus, a cDNA reverse transcribed from a transcript, an RNA transcribed from that cDNA, a DNA amplified from the cDNA, an RNA transcribed from the amplified DNA, etc., are all derived from the transcript and detection of such derived products is indicative of the presence and/or abundance of the original transcript in a sample. Thus, suitable samples include, but are not limited to, transcripts of the gene or genes, cDNA reverse transcribed from the transcript, cRNA transcribed from the cDNA, DNA amplified from the genes, RNA transcribed from amplified DNA, and the like.

Transcripts, as used herein, may include, but not limited to pre-mRNA nascent transcript(s), transcript processing intermediates, mature mRNA(s) and degradation products. It is not necessary to monitor all types of transcripts to practice this invention. For example, one may choose to practice the invention to measure the mature mRNA levels only.

In one embodiment, such sample is a homogenate of cells or tissues or other biological samples. Preferably, such sample is a total RNA preparation of a biological sample. More preferably in some embodiments, such a nucleic acid sample is the total mRNA isolated from a biological sample. Those of skill in the art will appreciate that the total mRNA prepared with most methods includes not only the mature mRNA, but also the RNA processing intermediates and nascent pre-mRNA transcripts. For example, total mRNA purified with a poly (dT) column contains RNA molecules with poly (A) tails. Those polyA$^+$ RNA molecules could be mature mRNA, RNA processing intermediates, nascent transcripts or degradation intermediates.

Biological samples may be of any biological tissue or fluid or cells from any organism. Frequently the sample will be a "clinical sample" which is a sample derived from a patient. Clinical samples provide a rich source of information regarding the various states of genetic network or gene expression. Some embodiments of the invention are employed to detect mutations and to identify the phenotype of mutations. Such embodiments have extensive applications in clinical diagnostics and clinical studies. Typical clinical samples include, but are not limited to, sputum, blood, blood cells (e.g., white cells), tissue or fine needle biopsy samples, urine, peritoneal fluid, and pleural fluid, or cells therefrom. Biological samples may also include sections of tissues, such as frozen sections or formalin fixed sections taken for histological purposes.

Another typical source of biological samples are cell cultures where gene expression states can be manipulated to explore the relationship among genes. In one aspect of the invention, methods are provided to generate biological samples reflecting a wide variety of states of the genetic network.

One of skill in the art would appreciate that it is desirable to inhibit or destroy RNase present in homogenates before homogenates can be used for hybridization. Methods of inhibiting or destroying nucleases are well known in the art. In some preferred embodiments, cells or tissues are homogenized in the presence of chaotropic agents to inhibit nuclease. In some other embodiments, RNase is inhibited or destroyed by heat treatment followed by proteinase treatment.

Methods of isolating total mRNA are also well known to those of skill in the art. For example, methods of isolation and purification of nucleic acids are described in detail in Chapter 3 of *Laboratory Techniques in Biochemistry and Molecular Biology: Hybridization With Nucleic Acid Probes, Part I. Theory and Nucleic Acid Preparation,* P. Tijssen, ed. Elsevier, N.Y. (1993) and Chapter 3 of *Laboratory Techniques in Biochemistry and Molecular Biology: Hybridization With Nucleic Acid Probes, Part I. Theory and Nucleic Acid Preparation,* P. Tijssen, ed. Elsevier, N.Y. (1993)).

In a preferred embodiment, the total RNA is isolated from a given sample using, for example, an acid guanidinium-phenol-chloroform extraction method and polyA$^+$ mRNA is isolated by oligo(dT) column chromatography or by using (dT) on magnetic beads (see, e.g., Sambrook et al., *Molecular Cloning: A Laboratory Manual* (2nd ed.), Vols. 1–3, Cold Spring Harbor Laboratory, (1989), or *Current Protocols in Molecular Biology,* F. Ausubel et al., ed. Greene Publishing and Wiley-Interscience, New York (1987)).

Frequently, it is desirable to amplify the nucleic acid sample prior to hybridization. One of skill in the art will appreciate that whatever amplification method is used, if a quantitative result is desired, care must be taken to use a method that maintains or controls for the relative frequencies of the amplified nucleic acids to achieve quantitative amplification.

Methods of "quantitative" amplification are well known to those of skill in the art. For example, quantitative PCR involves simultaneously co-amplifying a known quantity of a control sequence using the same primers. This provides an internal standard that may be used to calibrate the PCR reaction. The high density array may then include probes specific to the internal standard for quantification of the amplified nucleic acid.

One preferred internal standard is a synthetic AW106 cRNA. The AW106 cRNA is combined with RNA isolated from the sample according to standard techniques known to those of skilled in the art. The RNA is then reverse transcribed using a reverse transcriptase to provide copy DNA. The cDNA sequences are then amplified (e.g., by PCR) using labeled primers. The amplification products are separated, typically by electrophoresis, and the amount of radioactivity (proportional to the amount of amplified product) is determined. The amount of mRNA in the sample is then calculated by comparison with the signal produced by the known AW106 RNA standard. Detailed protocols for quantitative PCR are provided in *PCR Protocols, A Guide to Methods and Applications,* Innis et al., Academic Press, Inc. N.Y., (1990).

Other suitable amplification methods include, but are not limited to polymerase chain reaction (PCR) (Innis, et al., *PCR Protocols. A guide to Methods and Application.* Academic Press, Inc. San Diego, (1990)), ligase chain reaction (LCR) (see Wu and Wallace, *Genomics,* 4: 560 (1989), Landegren, et al., *Science,* 241: 1077 (1988) and Barringer, et al, *Gene,* 89: 117 (1990), transcription amplification (Kwoh, et al., *Proc. Natl. Acad. Sci. USA,* 86: 1173 (1989)), and self-sustained sequence replication (Guatelli, et al., *Proc. Nat. Acad. Sci. USA,* 87: 1874 (1990)).

Cell lysates or tissue homogenates often contain a number of inhibitors of polymerase activity. Therefore, RT-PCR typically incorporates preliminary steps to isolate total RNA or mRNA for subsequent use as an amplification template. A one-tube mRNA capture method may be used to prepare poly(A)⁺RNA samples suitable for immediate RT-PCR in the same tube (Boehringer Mannheim). The captured mRNA can be directly subjected to RT-PCR by adding a reverse transcription mix and, subsequently, a PCR mix.

In a particularly preferred embodiment, the sample mRNA is reverse transcribed with a reverse transcriptase and a primer consisting of oligo(dT) and a sequence encoding the phage T7 promoter to provide single stranded DNA template. The second DNA strand is polymerized using a DNA polymerase. After synthesis of double-stranded cDNA, T7 RNA polymerase is added and RNA is transcribed from the cDNA template. Successive rounds of transcription from each single cDNA template results in amplified RNA. Methods of in vitro polymerization are well known to those of skill in the art (see, e.g., Sambrook, supra.) and this particular method is described in detail by Van Gelder, et al., *Proc. Natl. Acad. Sci. USA*, 87: 1663–1667 (1990) who demonstrate that in vitro amplification according to this method preserves the relative frequencies of the various RNA transcripts. Moreover, Eberwine et al. *Proc. Natl. Acad. Sci. USA*, 89: 3010–3014 provide a protocol that uses two rounds of amplification via in vitro transcription to achieve greater than $10^6$ fold amplification of the original starting material, thereby permitting expression monitoring even where biological samples are limited.

It will be appreciated by one of skill in the art that the direct transcription method described above provides an antisense (aRNA) pool. Where antisense RNA is used as the target nucleic acid, the oligonucleotide probes provided in the array are chosen to be complementary to subsequences of the antisense nucleic acids. Conversely, where the target nucleic acid pool is a pool of sense nucleic acids, the oligonucleotide probes are selected to be complementary to subsequences of the sense nucleic acids. Finally, where the nucleic acid pool is double stranded, the probes may be of either sense as the target nucleic acids include both sense and antisense strands.

The protocols cited above include methods of generating pools of either sense or antisense nucleic acids. Indeed, one approach can be used to generate either sense or antisense nucleic acids as desired. For example, the cDNA can be directionally cloned into a vector (e.g., Stratagene's p Bluscript II KS (+) phagemid) such that it is flanked by the T3 and T7 promoters. In vitro transcription with the T3 polymerase will produce RNA of one sense (the sense depending on the orientation of the insert), while in vitro transcription with the T7 polymerase will produce RNA having the opposite sense. Other suitable cloning systems include phage lambda vectors designed for Cre-loxP plasmid subcloning (see e.g., Palazzolo et al., *Gene*, 88: 25–36 (1990)).

(B) Hybridizing Nucleic Acids to High Density Arrays

1. Probe Design

One of skill in the art will appreciate that an enormous number of array designs are suitable for the practice of this invention. The high density array will typically include a number of probes that specifically hybridize to the sequences of interest. In addition, in a preferred embodiment, the array will include one or more control probes.

The high density array chip includes "test probes." Test probes could be oligonucleotides that range from about 5 to about 45 or 5 to about 500 nucleotides, more preferably from about 10 to about 40 nucleotides and most preferably from about 15 to about 40 nucleotides in length. In other particularly preferred embodiments the probes are 20 or 25 nucleotides in length. In another preferred embodiments, test probes are double or single strand DNA sequences. DNA sequences are isolated or cloned from nature sources or amplified from nature sources using nature nucleic acid as templates. These probes have sequences complementary to particular subsequences of the genes whose expression they are designed to detect. Thus, the test probes are capable of specifically hybridizing to the target nucleic acid they are to detect.

In addition to test probes that bind the target nucleic acid(s) of interest, the high density array can contain a number of control probes. The control probes fall into three categories referred to herein as 1) normalization controls; 2) expression level controls; and 3) mismatch controls.

Normalization controls are oligonucleotide or other nucleic acid probes that are complementary to labeled reference oligonucleotides or other nucleic acid sequences that are added to the nucleic acid sample. The signals obtained from the normalization controls after hybridization provide a control for variations in hybridization conditions, label intensity, "reading" efficiency and other factors that may cause the signal of a perfect hybridization to vary between arrays. In a preferred embodiment, signals (e.g., fluorescence intensity) read from all other probes in the array are divided by the signal (e.g., fluorescence intensity) from the control probes thereby normalizing the measurements.

Virtually any probe may serve as a normalization control. However, it is recognized that hybridization efficiency varies with base composition and probe length. Preferred normalization probes are selected to reflect the average length of the other probes present in the array, however, they can be selected to cover a range of lengths. The normalization control(s) can also be selected to reflect the (average) base composition of the other probes in the array, however in a preferred embodiment, only one or a few normalization probes are used and they are selected such that they hybridize well (i.e. no secondary structure) and do not match any target-specific probes.

Expression level controls are probes that hybridize specifically with constitutively expressed genes in the biological sample. Virtually any constitutively expressed gene provides a suitable target for expression level controls. Typically expression level control probes have sequences complementary to subsequences of constitutively expressed "housekeeping genes" including, but not limited to the β-actin gene, the transferrin receptor gene, the GAPDH gene, and the like.

Mismatch controls may also be provided for the probes to the target genes, for expression level controls or for normalization controls. Mismatch controls are oligonucleotide probes or other nucleic acid probes identical to their corresponding test or control probes except for the presence of one or more mismatched bases. A mismatched base is a base selected so that it is not complementary to the corresponding base in the target sequence to which the probe would otherwise specifically hybridize. One or more mismatches are selected such that under appropriate hybridization conditions (e.g. stringent conditions) the test or control probe would be expected to hybridize with its target sequence, but the mismatch probe would not hybridize (or would hybridize to a significantly lesser extent). Preferred mismatch probes contain a central mismatch. Thus, for example, where a probe is a 20 mer, a corresponding mismatch probe will have the identical sequence except for a single base mismatch (e.g., substituting a G, a C or a T for an A) at any of positions 6 through 14 (the central mismatch).

Mismatch probes thus provide a control for non-specific binding or cross-hybridization to a nucleic acid in the sample other than the target to which the probe is directed.

Mismatch probes thus indicate whether a hybridization is specific or not. For example, if the target is present the perfect match probes should be consistently brighter than the mismatch probes. In addition, if all central mismatches are present, the mismatch probes can be used to detect a mutation. The difference in intensity between the perfect match and the mismatch probe (I(PM)-I(MM)) provides a good measure of the concentration of the hybridized material.

The high density array may also include sample preparation/amplification control probes. These are probes that are complementary to subsequences of control genes selected because they do not normally occur in the nucleic acids of the particular biological sample being assayed. Suitable sample preparation/amplification control probes include, for example, probes to bacterial genes (e.g., Bio B) where the sample in question is a biological from a eukaryote.

The RNA sample is then spiked with a known amount of the nucleic acid to which the sample preparation/amplification control probe is directed before processing. Quantification of the hybridization of the sample preparation/amplification control probe then provides a measure of alteration in the abundance of the nucleic acids caused by processing steps (e.g. PCR, reverse transcription, in vitro transcription, etc.).

In a preferred embodiment, oligonucleotide probes in the high density array are selected to bind specifically to the nucleic acid target to which they are directed with minimal non-specific binding or cross-hybridization under the particular hybridization conditions utilized. Because the high density arrays of this invention can contain in excess of 1,000,000 different probes, it is possible to provide every probe of a characteristic length that binds to a particular nucleic acid sequence. Thus, for example, the high density array can contain every possible 20-mer sequence complementary to an IL-2 mRNA.

However, there may exist 20-mer subsequences that are not unique to the IL-2 mRNA. Probes directed to these subsequences are expected to cross-hybridize with occurrences of their complementary sequence in other regions of the sample genome. Similarly, other probes simply may not hybridize effectively under the hybridization conditions (e.g., due to secondary structure, or interactions with the substrate or other probes). Thus, in a preferred embodiment, the probes that show such poor specificity or hybridization efficiency are identified and may not be included either in the high density array itself (e.g., during fabrication of the array) or in the post-hybridization data analysis.

In addition, in a preferred embodiment, expression monitoring arrays are used to identify the presence and expression (transcription) level of genes which are several hundred base pairs long. For most applications it would be useful to identify the presence, absence, or expression level of several thousand to one hundred thousand genes. Because the number of oligonucleotides per array is limited in a preferred embodiment, it is desired to include only a limited set of probes specific to each gene whose expression is to be detected.

As disclosed in U.S. application Ser. No. 08/772,376, probes as short as 15, 20, or 25 nucleotide are sufficient to hybridize to a subsequence of a gene and that, for most genes, there is a set of probes that performs well across a wide range of target nucleic acid concentrations. In a preferred embodiment, it is desirable to choose a preferred or "optimum" subset of probes for each gene before synthesizing the high density array.

2. Forming High Density Arrays

Methods of forming high density arrays of oligonucleotides, peptides and other polymer sequences with a minimal number of synthetic steps are known. The oligonucleotide analogue array can be synthesized on a solid substrate by a variety of methods, including, but not limited to, light-directed chemical coupling, and mechanically directed coupling. See Pirrung et al., U.S. Pat. No. 5,143,854 (see also PCT Application No. WO 90/15070) and Fodor et al., PCT Publication Nos. WO 92/10092 and WO 93/09668 and U.S. Ser. No. 07/980,523 which disclose methods of forming vast arrays of peptides, oligonucleotides and other molecules using, for example, light-directed synthesis techniques. See also, Fodor et al., *Science,* 251, 767–77 (1991). These procedures for synthesis of polymer arrays are now referred to as VLSIPS™ procedures. Using the VLSIPS™ approach, one heterogeneous array of polymers is converted, through simultaneous coupling at a number of reaction sites, into a different heterogeneous array. See, U.S. application Ser. Nos. 07/796,243 and 07/980,523.

The development of VLSIPS™ technology as described in the above-noted U.S. Pat. No. 5,143,854 and PCT patent publication Nos. WO 90/15070 and 92/10092, is considered pioneering technology in the fields of combinatorial synthesis and screening of combinatorial libraries. More recently, patent application Ser. No. 08/082,937, filed Jun. 25, 1993, describes methods for making arrays of oligonucleotide probes that can be used to check or determine a partial or complete sequence of a target nucleic acid and to detect the presence of a nucleic acid containing a specific oligonucleotide sequence.

In brief, the light-directed combinatorial synthesis of oligonucleotide arrays on a glass surface proceeds using automated phosphoramidite chemistry and chip masking techniques. In one specific implementation, a glass surface is derivatized with a silane reagent containing a functional group, e.g., a hydroxyl or amine group blocked by a photolabile protecting group. Photolysis through a photolithogaphic mask is used selectively to expose functional groups which are then ready to react with incoming 5'-photoprotected nucleoside phosphoramidites. The phosphoramidites react only with those sites which are illuminated (and thus exposed by removal of the photolabile blocking group). Thus, the phosphoramidites only add to those areas selectively exposed from the preceding step. These steps are repeated until the desired array of sequences have been synthesized on the solid surface. Combinatorial synthesis of different oligonucleotide analogues at different locations on the array is determined by the pattern of illumination during synthesis and the order of addition of coupling reagents.

In the event that an oligonucleotide analogue with a polyamide backbone is used in the VLSIPS™ procedure, it is generally inappropriate to use phosphoramidite chemistry to perform the synthetic steps, since the monomers do not attach to one another via a phosphate linkage. Instead, peptide synthetic methods are substituted. See, e.g., Pirrung et al. U.S. Pat. No. 5,143,854.

Peptide nucleic acids are commercially available from, e.g., Biosearch, Inc. (Bedford, Mass.) which comprise a polyamide backbone and the bases found in naturally occurring nucleosides. Peptide nucleic acids are capable of binding to nucleic acids with high specificity, and are considered "oligonucleotide analogues" for purposes of this disclosure.

In addition to the foregoing, additional methods which can be used to generate an array of oligonucleotides on a single substrate are described in co-pending applications Ser. No. 07/980,523, filed Nov. 20, 1992, and 07/796,243, filed Nov. 22, 1991 and in PCT Publication No. WO 93/09668. In the methods disclosed in these applications, reagents are delivered to the substrate by either (1) flowing within a channel defined on predefined regions or (2) "spotting" on predefined regions or (3) through the use of photoresist. However, other approaches, as well as combinations of spotting and flowing, may be employed. In each instance, certain activated regions of the substrate are mechanically separated from other regions when the monomer solutions are delivered to the various reaction sites.

A typical "flow channel" method applied to the compounds and libraries of the present invention can generally be described as follows. Diverse polymer sequences are synthesized at selected regions of a substrate or solid support by forming flow channels on a surface of the substrate through which appropriate reagents flow or in which appropriate reagents are placed. For example, assume a monomer "A" is to be bound to the substrate in a first group of selected regions. If necessary, all or part of the surface of the substrate in all or a part of the selected regions is activated for binding by, for example, flowing appropriate reagents through all or some of the channels, or by washing the entire substrate with appropriate reagents. After placement of a channel block on the surface of the substrate, a reagent having the monomer A flows through or is placed in all or some of the channel(s). The channels provide fluid contact to the first selected regions, thereby binding the monomer A on the substrate directly or indirectly (via a spacer) in the first selected regions.

Thereafter, a monomer B is coupled to second selected regions, some of which may be included among the first selected regions. The second selected regions will be in fluid contact with a second flow channel(s) through translation, rotation, or replacement of the channel block on the surface of the substrate; through opening or closing a selected valve; or through deposition of a layer of chemical or photoresist. If necessary, a step is performed for activating at least the second regions. Thereafter, the monomer B is flowed through or placed in the second flow channel(s), binding monomer B at the second selected locations. In this particular example, the resulting sequences bound to the substrate at this stage of processing will be, for example, A, B, and AB. The process is repeated to form a vast array of sequences of desired length at known locations on the substrate.

After the substrate is activated, monomer A can be flowed through some of the channels, monomer B can be flowed through other channels, a monomer C can be flowed through still other channels, etc. In this manner, many or all of the reaction regions are reacted with a monomer before the channel block must be moved or the substrate must be washed and/or reactivated. By making use of many or all of the available reaction regions simultaneously, the number of washing and activation steps can be minimized.

One of skill in the art will recognize that there are alternative methods of forming channels or otherwise protecting a portion of the surface of the substrate. For example, according to some embodiments, a protective coating such as a hydrophilic or hydrophobic coating (depending upon the nature of the solvent) is utilized over portions of the substrate to be protected, sometimes in combination with materials that facilitate wetting by the reactant solution in other regions. In this manner, the flowing solutions are further prevented from passing outside of their designated flow paths.

High density nucleic acid arrays can be fabricated by depositing presynthesized or natural nucleic acids in predetermined positions. Synthesized or natural nucleic acids are deposited on specific locations of a substrate by light directed targeting and oligonucleotide directed targeting. Nucleic acids can also be directed to specific locations in much the same manner as the flow channel methods. For example, a nucleic acid A can be delivered to and coupled with a first group of reaction regions which have been appropriately activated. Thereafter, a nucleic acid B can be delivered to and reacted with a second group of activated reaction regions. Nucleic acids are deposited in selected regions. Another embodiment uses a dispenser that moves from region to region to deposit nucleic acids in specific spots. Typical dispensers include a micropipette or capillary pin to deliver nucleic acid to the substrate and a robotic system to control the position of the micropipette with respect to the substrate. In other embodiments, the dispenser includes a series of tubes, a manifold, an array of pipettes or capillary pins, or the like so that various reagents can be delivered to the reaction regions simultaneously.

3. Hybridization

Nucleic acid hybridization simply involves contacting a probe and target nucleic acid under conditions where the probe and its complementary target can form stable hybrid duplexes through complementary base pairing. The nucleic acids that do not form hybrid duplexes are then washed away leaving the hybridized nucleic acids to be detected, typically through detection of an attached detectable label. It is generally recognized that nucleic acids are denatured by increasing the temperature or decreasing the salt concentration of the buffer containing the nucleic acids. Under low stringency conditions (e.g., low temperature and/or high salt) hybrid duplexes (e.g., DNA:DNA, RNA:RNA, or RNA:DNA) will form even where the annealed sequences are not perfectly complementary. Thus specificity of hybridization is reduced at lower stringency. Conversely, at higher stringency (e.g., higher temperature or lower salt) successful hybridization requires fewer mismatches.

One of skill in the art will appreciate that hybridization conditions may be selected to provide any degree of stringency. In a preferred embodiment, hybridization is performed at low stringency in this case in 6×SSPE-T at 37 C. (0.005% Triton X-100) to ensure hybridization and then subsequent washes are performed at higher stringency (e.g., 1×SSPE-T at 37 C.) to eliminate mismatched hybrid duplexes. Successive washes may be performed at increasingly higher stringency (e.g., down to as low as 0.25× SSPE-T at 37 C. to 50 C.) until a desired level of hybridization specificity is obtained. Stringency can also be increased by addition of agents such as formamide. Hybridization specificity may be evaluated by comparison of hybridization to the test probes with hybridization to the various controls that can be present (e.g., expression level control, normalization control, mismatch controls, etc.).

In general, there is a tradeoff between hybridization specificity (stringency) and signal intensity. Thus, in a preferred embodiment, the wash is performed at the highest stringency that produces consistent results and that provides a signal intensity greater than approximately 10% of the background intensity. Thus, in a preferred embodiment, the hybridized array may be washed at successively higher stringency solutions and read between each wash. Analysis of the data sets thus produced will reveal a wash stringency above which the hybridization pattern is not appreciably altered and which provides adequate signal for the particular oligonucleotide probes of interest.

In a preferred embodiment, background signal is reduced by the use of a detergent (e.g., C-TAB) or a blocking reagent (e.g., sperm DNA, cot-1 DNA, etc.) during the hybridization to reduce non-specific binding. In a particularly preferred embodiment, the hybridization is performed in the presence of about 0.5 mg/ml DNA (e.g., herring sperm DNA). The use of blocking agents in hybridization is well known to those of skill in the art (see, e.g., Chapter 8 in P. Tijssen, supra.)

The stability of duplexes formed between RNAs or DNAs are generally in the order of RNA:RNA>RNA:DNA>DNA:DNA, in solution. Long probes have better duplex stability with a target, but poorer mismatch discrimination than shorter probes (mismatch discrimination refers to the measured hybridization signal ratio between a perfect match probe and a single base mismatch probe). Shorter probes (e.g., 8-mers) discriminate mismatches very well, but the overall duplex stability is low.

Altering the thermal stability ($T_m$) of the duplex formed between the target and the probe using, e.g., known oligonucleotide analogues allows for optimization of duplex stability and mismatch discrimination. One useful aspect of altering the $T_m$ arises from the fact that adenine-thymine (A-T) duplexes have a lower $T_m$ than guanine-cytosine (G-C) duplexes, due in part to the fact that the A-T duplexes have 2 hydrogen bonds per base-pair, while the G-C duplexes have 3 hydrogen bonds per base pair. In heterogeneous oligonucleotide arrays in which there is a non-uniform distribution of bases, it is not generally possible to optimize hybridization for each oligonucleotide probe simultaneously. Thus, in some embodiments, it is desirable to selectively destabilize G-C duplexes and/or to increase the stability of A-T duplexes. This can be accomplished, e.g., by substituting guanine residues in the probes of an array which form G-C duplexes with hypoxanthine, or by substituting adenine residues in probes which form A-T duplexes with 2,6 diaminopurine or by using the salt tetramethyl ammonium chloride (TMACl) in place of NaCl.

Altered duplex stability conferred by using oligonucleotide analogue probes can be ascertained by following, e.g., fluorescence signal intensity of oligonucleotide analogue arrays hybridized with a target oligonucleotide over time. The data allow optimization of specific hybridization conditions at, e.g., room temperature (for simplified diagnostic applications in the future).

Another way of verifying altered duplex stability is by following the signal intensity generated upon hybridization with time. Previous experiments using DNA targets and DNA chips have shown that signal intensity increases with time, and that the more stable duplexes generate higher signal intensities faster than less stable duplexes. The signals reach a plateau or "saturate" after a certain amount of time due to all of the binding sites becoming occupied. These data allow for optimization of hybridization, and determination of the best conditions at a specified temperature.

Methods of optimizing hybridization conditions are well known to those of skill in the art (see, e.g., *Laboratory Techniques in Biochemistry and Molecular Biology, Vol. 24: Hybridization With Nucleic Acid Probes*, P. Tijssen, ed. Elsevier, N.Y., (1993)).

(C) Signal Detection

In a preferred embodiment, the hybridized nucleic acids are detected by detecting one or more labels attached to the sample nucleic acids. The labels may be incorporated by any of a number of means well known to those of skill in the art. However, in a preferred embodiment, the label is simultaneously incorporated during the amplification step in the preparation of the sample nucleic acids. Thus, for example, polymerase chain reaction (PCR) with labeled primers or labeled nucleotides will provide a labeled amplification product. In a preferred embodiment, transcription amplification, as described above, using a labeled nucleotide (e.g. fluorescein-labeled UTP and/or CTP) incorporates a label into the transcribed nucleic acids.

Alternatively, a label may be added directly to the original nucleic acid sample (e.g., mRNA, polyA mRNA, cDNA, etc.) or to the amplification product after the amplification is completed. Means of attaching labels to nucleic acids are well known to those of skill in the art and include, for example nick translation or end-labeling (e.g. with a labeled RNA) by kinasing of the nucleic acid and subsequent attachment (ligation) of a nucleic acid linker joining the sample nucleic acid to a label (e.g., a fluorophore).

Detectable labels suitable for use in the present invention include any composition detectable by spectroscopic, photochemical, biochemical, immunochemical, electrical, optical or chemical means. Useful labels in the present invention include biotin for staining with labeled streptavidin conjugate, magnetic beads (e.g., Dynabeads™), fluorescent dyes (e.g. fluorescein, texas red, rhodamine, green fluorescent protein, and the like), radiolabels (e.g., $^3H$, $^{125}I$, $^{35}S$, $^{14}C$, or $^{32}P$), enzymes (e.g., horse radish peroxidase, alkaline phosphatase and others commonly used in an ELISA), and colorimetric labels such as colloidal gold or colored glass or plastic (e.g., polystyrene, polypropylene, latex, etc.) beads. Patents teaching the use of such labels include U.S. Pat. Nos. 3,817,837; 3,850,752; 3,939,350; 3,996,345; 4,277,437; 4,275,149; and 4,366,241.

Means of detecting such labels are well known to those of skill in the art. Thus, for example, radiolabels may be detected using photographic film or scintillation counters, fluorescent markers may be detected using a photodetector to detect emitted light. Enzymatic labels are typically detected by providing the enzyme with a substrate and detecting the reaction product produced by the action of the enzyme on the substrate, and colorimetric labels are detected by simply visualizing the colored label. One particular preferred methods uses colloidal gold label that can be detected by measuring scattered light.

The label may be added to the target (sample) nucleic acid(s) prior to, or after the hybridization. So called "direct labels" are detectable labels that are directly attached to or incorporated into the target (sample) nucleic acid prior to hybridization. In contrast, so called "indirect labels" are joined to the hybrid duplex after hybridization. Often, the indirect label is attached to a binding moiety that has been attached to the target nucleic acid prior to the hybridization. Thus, for example, the target nucleic acid may be biotinylated before the hybridization. After hybridization, an avidin-conjugated fluorophore will bind the biotin bearing hybrid duplexes providing a label that is easily detected. For a detailed review of methods of labeling nucleic acids and detecting labeled hybridized nucleic acids see *Laboratory Techniques in Biochemistry and Molecular Biology, Vol. 24: Hybridization With Nucleic Acid Probes*, P. Tijssen, ed. Elsevier, N.Y., (1993)).

Fluorescent labels are preferred and easily added during an in vitro transcription reaction. In a preferred embodiment, fluorescein labeled UTP and CTP are incorporated into the RNA produced in an in vitro transcription reaction as described above.

Means of detecting labeled target (sample) nucleic acids hybridized to the probes of the high density array are known to those of skill in the art. Thus, for example, where a calorimetric label is used, simple visualization of the label is sufficient. Where a radioactive labeled probe is used, detection of the radiation (e.g. with photographic film or a solid state detector) is sufficient.

In a preferred embodiment, however, the target nucleic acids are labeled with a fluorescent label and the localization of the label on the probe array is accomplished with fluorescent microscopy. The hybridized array is excited with a light source at the excitation wavelength of the particular fluorescent label and the resulting fluorescence at the emission wavelength is detected. In a particularly preferred embodiment, the excitation light source is a laser appropriate for the excitation of the fluorescent label.

The confocal microscope may be automated with a computer-controlled stage to automatically scan the entire high density array. Similarly, the microscope may be equipped with a phototransducer (e.g., a photomultiplier, a solid state array, a CCD camera, etc.) attached to an automated data acquisition system to automatically record the fluorescence signal produced by hybridization to each oligonucleotide probe on the array. Such automated systems are described at length in U.S. Pat. No. 5,143,854, PCT Application 20 92/10092, and copending U.S. application Ser. No. 08/195,889 filed on Feb. 10, 1994. Use of laser illumination in conjunction with automated confocal microscopy for signal detection permits detection at a resolution of better than about 100 µm, more preferably better than about 50 µm, and most preferably better than about 25 µm.

One of skill in the art will appreciate that methods for evaluating the hybridization results vary with the nature of the specific probe nucleic acids used as well as the controls provided. In the simplest embodiment, simple quantification of the fluorescence intensity for each probe is determined. This is accomplished simply by measuring probe signal strength at each location (representing a different probe) on the high density array (e.g., where the label is a fluorescent label, detection of the amount of florescence (intensity) produced by a fixed excitation illumination at each location on the array). Comparison of the absolute intensities of an array hybridized to nucleic acids from a "test" sample with intensities produced by a "control" sample provides a measure of the relative expression of the nucleic acids that hybridize to each of the probes.

One of skill in the art, however, will appreciate that hybridization signals will vary in strength with efficiency of hybridization, the amount of label on the sample nucleic acid and the amount of the particular nucleic acid in the sample. Typically nucleic acids present at very low levels (e.g., <1 pM) will show a very weak signal. At some low level of concentration, the signal becomes virtually indistinguishable from background. In evaluating the hybridization data, a threshold intensity value may be selected below which a signal is not counted as being essentially indistinguishable from background.

Where it is desirable to detect nucleic acids expressed at lower levels, a lower threshold is chosen. Conversely, where only high expression levels are to be evaluated a higher threshold level is selected. In a preferred embodiment, a suitable threshold is about 10% above that of the average background signal.

In addition, the provision of appropriate controls permits a more detailed analysis that controls for variations in hybridization conditions, cell health, non-specific binding and the like. Thus, for example, in a preferred embodiment, the hybridization array is provided with normalization controls. These normalization controls are probes complementary to control sequences added in a known concentration to the sample. Where the overall hybridization conditions are poor, the normalization controls will show a smaller signal reflecting reduced hybridization. Conversely, where hybridization conditions are good, the normalization controls will provide a higher signal reflecting the improved hybridization. Normalization of the signal derived from other probes in the array to the normalization controls thus provides a control for variations in hybridization conditions. Typically, normalization is accomplished by dividing the measured signal from the other probes in the array by the average signal produced by the normalization controls. Normalization may also include correction for variations due to sample preparation and amplification. Such normalization may be accomplished by dividing the measured signal by the average signal from the sample preparation/amplification control probes (e.g., the Bio B probes). The resulting values may be multiplied by a constant value to scale the results.

As indicated above, the high density array can include mismatch controls. In a preferred embodiment, there is a mismatch control having a central mismatch for every probe (except the normalization controls) in the array. It is expected that after washing in stringent conditions, where a perfect match would be expected to hybridize to the probe, but not to the mismatch, the signal from the mismatch controls should only reflect non-specific binding or the presence in the sample of a nucleic acid that hybridizes with the mismatch. Where both the probe in question and its corresponding mismatch control both show high signals, or the mismatch shows a higher signal than its corresponding test probe, there is a problem with the hybridization and the signal from those probes is ignored. The difference in hybridization signal intensity between the target specific probe and its corresponding mismatch control is a measure of the discrimination of the target-specific probe. Thus, in a preferred embodiment, the signal of the mismatch probe is subtracted from the signal from its corresponding test probe to provide a measure of the signal due to specific binding of the test probe.

The concentration of a particular sequence can then be determined by measuring the signal intensity of each of the probes that bind specifically to that gene and normalizing to the normalization controls. Where the signal from the probes is greater than the mismatch, the mismatch is subtracted. Where the mismatch intensity is equal to or greater than its corresponding test probe, the signal is ignored. The expression level of a particular gene can then be scored by the number of positive signals (either absolute or above a threshold value), the intensity of the positive signals (either absolute or above a selected threshold value), or a combination of both metrics (e.g., a weighted average).

In some preferred embodiments, a computer system is used to compare the hybridization intensities of the perfect match and mismatch probes of each pair. If the gene is expressed, the hybridization intensity (or affinity) of a perfect match probe of a pair should be recognizably higher than the corresponding mismatch probe. Generally, if the hybridizations intensities of a pair of probes are substantially the same, it may indicate the gene is not expressed. However, the determination is not based on a single pair of probes, the determination of whether a gene is expressed is based on an analysis of many pairs of probes.

After the system compares the hybridization intensity of the perfect match and mismatch probes, the system indicates expression of the gene. As an example, the system may indicate to a user that the gene is either present (expressed), marginal or absent (unexpressed). Specific procedures for data analysis is disclosed in U.S. application Ser. No. 08/772,376, previously incorporated for all purposes.

In addition to high density nucleic acid arrays, other methods are also useful for massive gene expression monitoring. Differential display, described by Liang, P. and Pardee, A. B. (Differential Display of eukaryotic messenger RNA by means of the polymerase chain reaction. *Science* 257:967–971, 1992, incorporated herein by reference for all purposes) provides a useful mean for distinguishing gene expression between two samples. Serial analysis of gene expression, described by Velculescu et al. (Serial Analysis of Gene Expression. *Science,* 270:484–487, 1995, in corporated herein by reference for all purposes) provides another method for quantitative and qualitative analysis of gene expression. Optical fiber oligonucleotide sensors, described by Ferguson et al. (A Fiber-optic DNA biosensor microarray for the analysis of gene expression. Nature-Biotechnology 14:1681–1684, 1996), can also be used for gene expression monitoring.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference for all purposes.

EXAMPLES

Summary

Mechanistic insights to viral replication and pathogenesis generally have come from the analysis of viral gene products, either by studying their biochemical activities and interactions individually or by creating mutant viruses and analyzing their phenotype. Now it is possible to identify and catalog the host cell genes whose mRNA levels change in response to the pathogen. We have employed DNA array technology to monitor the level of approximately 6600 human mRNAs in uninfected as compared to human cytomegalovirus-infected cells. The level of 258 mRNAs changed by a factor of 4 or more early after infection, before the onset of viral DNA replication. Several of these mRNAs encode gene products that might play key roles in virus-induced pathogenesis, identifying them as intriguing targets for further study.

Introduction

Human cytomegalovirus (HCMV) has the potential to alter cellular gene expression though multiple mechanisms. Its initial interaction with the cell surface could initiate a regulatory signal; indeed, the virion gB and gH glycoproteins induce cellular transcription factors when added to uninfected cells (1). Constituents of the virion, such as the tegument protein, pp71, migrate to the nucleus and activate transcription after infection (2), and viral proteins synthesized after infection, such as the immediate early 1 and 2 proteins, modulate transcription (3–5). The virus encodes several G protein-coupled receptors (6,7) that likely initiate gene regulatory signal cascades in response to ligands, and HCMV infection has been shown to perturb cell cycle regulation (8–11), which leads to changes in cellular gene expression. The complex virus-host cell interaction has the potential to dramatically modulate the expression of cellular genes.

Relatively few cellular genes have been identified whose activity changes in HCMV-infected cells (12). Recently, we used differential display analysis to identify 15 interferon-inducible genes that are activated by the virus subsequent to infection (13). However, this screen identified only genes whose mRNA levels changed dramatically, and we were not able to perform the screen under a variety of conditions given its labor-intensive nature. In contrast to differential display, the DNA array assay is easily performed and can detect subtle changes in mRNA levels. We report the identification of 258 cellular mRNAs whose level changes by a factor of 4 or more before the onset of HCMV DNA replication.

Materials and Methods

Cells and Viruses. Primary human foreskin fibroblasts at passage 10–15 were cultured in DMEM containing 10% fetal calf serum. After the cells remained at confluence for thee days, they were infected at a multiplicity of 3 plaque-forming units per cell with HCMV AD169 or Toledo virions that were purified as described (14).

Sample preparation and analysis with DNA arrays. Biotinylated single-stranded antisense RNA samples for hybridization were prepared as described (15) with minor modifications. Total cellular RNA was prepared using the TRIZOL Reagent (GibcoBRL), polyadenylated RNA was isolated, and portions (5 $\mu$g) were used as the template for the first strand cDNA synthesis in a reaction that was primed with oligo (dT) containing a T7 RNA polymerase promoter sequence at its 5' end [5GGCCAGTGAATTGTAATACGACTCACTATAG GGAGCGG(T)$_{24}$-3'](SEQ ID NO: 1). The second cDNA strand was synthesized using E. coli DNA polymerase I and ligase. The resulting cDNA (0.5–1 $\mu$g) was used as template to make a biotinylated RNA probe by in vitro transcription using the T7 Megascript System (Ambion). Unincorporated nucleotides were removed using a G-50 Quick Spin Column (Boebringer Mannheim). The labeled RNA was fragmented to an average size of 50–100 bases by incubating at 94° C. for 30 mm in buffer containing 40mM Tris-Ac, pH8.1, 100 mM KOAc, and 30 mM MgQAc. The hybridization (15 h), washing and staining protocols were as described (15), and employed a set of four human gene chips (HUM6000 A, B, C and D, Affymetrix). The DNA arrays were scanned using a confocal scanner manufactured for Affymetrix by Molecular Dynamics.

Data analysis: The data collected in each hybridization experiment was processed using the GeneChip™ software supplied with the Affymetrix instrumentation system. To evaluate if RNA corresponding to each of the 6600 genes encoded on the array was detectable or undetectable a number of parameters were evaluated (15, 16), including the number of probe pairs interrogating each gene in which the intensity of the perfect match (PM) hybridization reaction exceeded that of the mismatch (MM) hybridization signal (cutoffs <45%) and the PM/MM ratios for each set of probe pairs. To determine the quantitative amounts of RNA from each gene, the average of the differences (PM-MM) for each probe pair in a probe set was calculated (cutoff >50) as well as the average differences across the probe sets (cutoff >10). The cutoff thresholds were determined empirically to be conservative, i.e., they minimized false positives. The change in the level of expression for any gene was considered significant if the change in the average differences across the probe sets was greater than 3-fold.

RNA analysis by Northern blot. GeneChip™ results were confirmed by Northern blot assay. Total RNA (3 $\mu$g) from mock-infected cells or cells infected with the HCMV AD169 or Toledo strains was subjected to electrophoresis, blotted to a membrane and probed with random hexanucleotide-primed $^{32}$P-labeled cDNA fragments from I.M.A.G.E. clones (Genome Systems, Inc.).

Results

The gene chip assay utilized a set of four probe arrays that together include oligonucleotides corresponding to more than 6600 human mRNAs (16). Each array (1.6 cm$^2$) contains more than 65,000 features, and a different oligodeoxyribonucleotide (25 bases) is synthesized on the surface of the derivatized glass wafer within the boundaries of each feature using light sensitive chemistry (17–21). The arrays contain 20 pairs of oligonucleotide probes corresponding to each RNA that is interrogated. Each probe pair consists of one 25-mer that is a perfect complement to the RNA (a perfect match probe) and a companion oligonucleotide that carries a single base difference in a central position (a mismatch probe). The mismatch probes serve as internal controls for hybridization specificity. Empirically derived rules used for the selection of oligonucleotide probes with the best sensitivity and specificity have been described (16).

RNA samples were prepared for analysis at 40 min, 8 h and 24 h after mock-infection or HCMV (strain AD169) infection of primary human fibroblasts. Under these conditions, HCMV DNA replication begins between 24–36 h after infection (10), and the complete viral replication cycle requires about 72 h. So all of the time points assayed were relatively early in the HCMV replication cycle. Biotinylated RNA target samples were generated by in vitro transcription of cDNA that was prepared from cellular mRNA using an oligo dT primer with a T7 polymerase promoter at its 5' end. This protocol amplifies the mRNA population in an unbiased and reproducible fashion (16). The resulting antisense RNA was fragmented to an average size of 50 to 100 bases, hybridized to the oligonucleotide probe arrays and then the arrays were reacted with phycoerythin-conjugated strepavidin. The intensity of the fluorescent signal within each feature was then quantified using a confocal scanner (Affymetrix). Previous studies have demonstrated that the fluorescent signal is linearly related to the concentration of RNA target within the range of about 1 (1 part in 300,000) to $10^3$ copies of RNA per cell (16). Above $10^3$ copies per cell, the signal continues to increase, but in a nonlinear fashion because the oligonucleotide probes begin to saturate. RNAs corresponding to 3020–3380 out of the 6600 genes were detected in different experiments. The range is due in part to virus-induced changes. However, much of the variation is due to mRNAs expressed at the 1–10 copy per cell level, scoring as present in one assay and absent in another experiment.

The DNA arrays contain a set of 198 oligonucleotides corresponding to sequences spread across the entire length of the GAPDH mRNA. The target RNAs prepared at 8 h after infection with HCMV (FIG. 1A) or after mock infection (data not shown) hybridized to the complete GAPDH probe set. The arrays also included oligonucleotides spanning the actin mRNA, and target RNAs hybridized to this complete probe set, as well (data not shown). These controls demonstrated that the target RNA preparations span the entire length of the test gene and provided confidence that the cDNA synthesis and subsequent in vitro transcription generated target RNAs representative of the input mRNA.

The reproducibility of hybridization signals produced by independent preparations of target RNAs also was tested. Biotinylated target RNA was prepared from mock-infected cells (FIG. 1B) or at 8 h after infection (FIG. 1C) and hybridized to different sets of arrays. The concentration of only one cellular mRNA differed by more than a factor of 3 in the replicate experiments (FIG. 1B). This control demonstrates that the hybridization signals observed in independent experiments are highly reproducible. Further, the two preparations of infected cell target RNAs were prepared from infected primary fibroblasts derived from two different tissue samples, ruling out the possibility that changes in RNA levels might reflect genetic differences in the host cells. Differences greater than 3-fold observed for hybridization signals in comparisons of mock-infected versus infected cells should identify genes whose mRNA levels change after infection.

Figure 2:
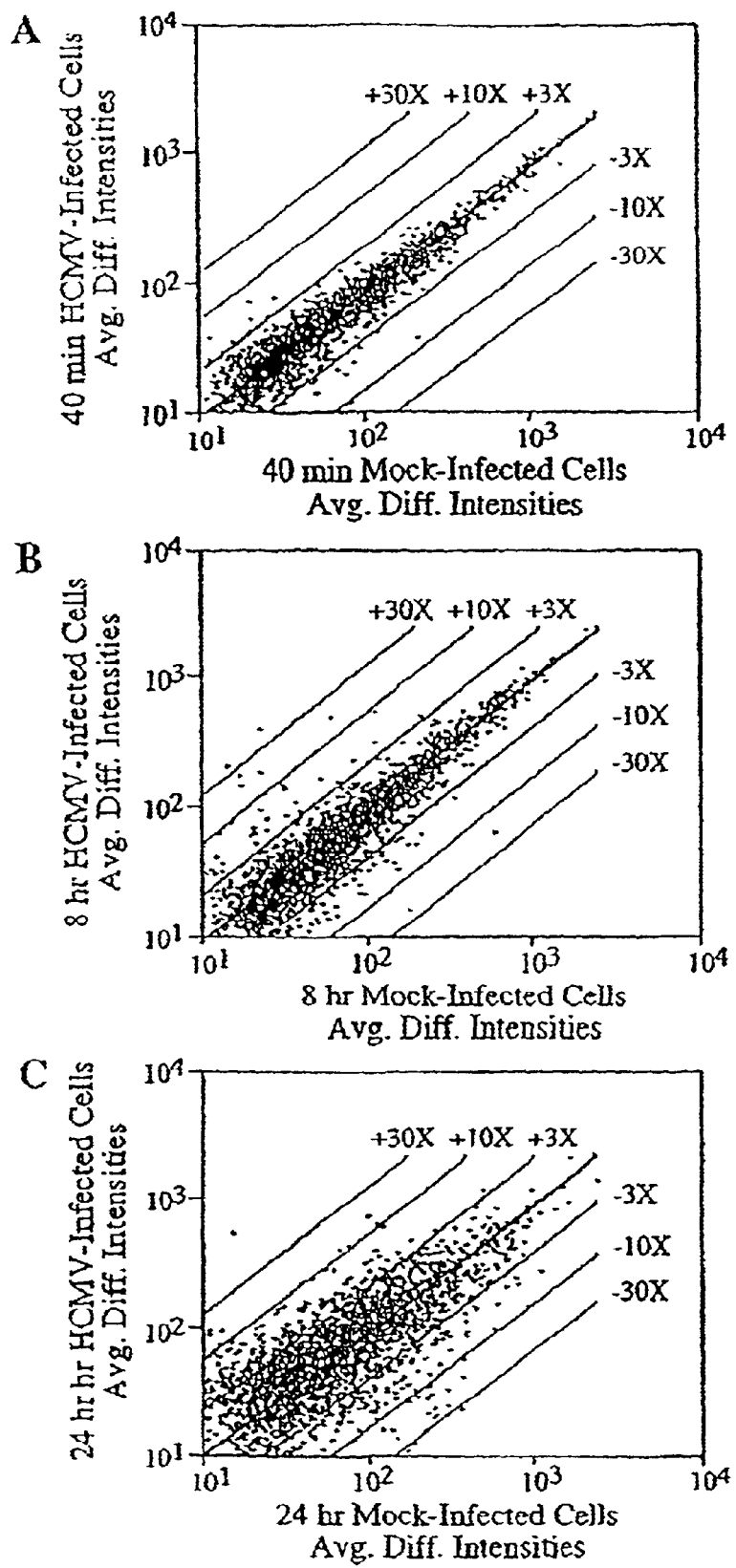

When target RNA preparations were compared at 40 min after mock or virus infection, the level of 27 mRNAs had changed in response to infection by a factor of thee or more; at 8 and 24 h after infection, the number of altered mRNAs increased to 93 and 364, respectively (FIG. 2). Applying a more stringent four-fold cut off, we generated a set of 258 mRNAs for further analysis (Table 1). Of these mRNAs, 124 in creased and 134 decreased after infection. We assume that most changes result from altered transcriptional regulation, but we have not yet tested this supposition. We confirmed 49 (40%) of the mRNAs predicted to be increased and 23 (17%) of the mRNAs predicted to be decreased either by northern blot analysis of independent RNA preparations (representative results in FIG. 3) or by reference to earlier studies that demonstrated a change. All attempts to confirm a predicted alteration in the group of 258 mRNAs were successful.

We assayed changes in mRNA levels for a total of 58 genes in this study by northern blot. When we performed these assays, we included RNA preparations from cells infected with HCMV strain AD169, the laboratory adapted strain used for the DNA array analysis, and HCMV strain Toledo, a clinical isolate that has not been extensively passaged in cultured cells (22). We observed the same alteration in mRNA level for both infections (representative results in FIG. 3). Although we might find some differences as more genes are assayed, our results to date argue that the laboratory and clinical isolates of HCMV alter cellular gene expression in a similar fashion.

Discussion

HCMV replicates in many different cell types within its infected host, some of which might respond to infection differently than the primary fibroblasts we have studied here. Keeping this caveat in mind, we nevertheless can speculate that several of the cellular genes whose mRNA levels change after infection of fibroblasts might profoundly influence HCMV replication and pathogenesis.

HLA-E mRNAs. In order to protect infected cells from cytotoxic T lymphocytes, multiple HCMV gene products act to reduce cell surface expression of classical class I MHC molecules (23–28). Although these viral activities protect infected cells from cytotoxic T lymphocytes, they also have the potential to render infected cells susceptible to natural killer (NK) cells that can recognize and destroy cells that no longer express class I MHC molecules. HLA-E mRNA is induced by a factor of 19 at 24 h after infection (Table 1), whereas HLA-A, HLA-D and HLA-G family members that were represented in the DNA arrays were not changed (data not shown). HLA-E is a nonclassical class I molecule whose cell surface expression requires that it bind peptides derived from the signal sequences of other class I molecules (HLA-A, -B and -C) (29). Recently, it has been shown that natural killer (NK) cells recognize and spare target cells expressing HLA-E on their surface (30, 31). This recognition is mediated by the NK cell CD94-NKG2 cell surface receptor. Assuming that the elevated mRNA leads to elevated cell surface expression of HLA-E, this modulation should protect virus-infected cells from NK cell killing. This would be the second mechanism by which HCMV avoids NK cell surveillance. The viral UL18 protein is an MHC homologue that engages another receptor (NKIR) on the NK cell to avoid attack (32).

Ro/SSA 52 kDa mRNA. HCMV-infected cells contain enhanced levels of the Ro/SSA 52 kDa protein (Table 1). This protein, which is a constituent of a ribonucleoprotein complex, is induced by a factor of 12 at 24 h after infection. Autoantibodies to this protein are found in a variety of connective tissue diseases: commonly in systemic lupus erythematosis, neonatal lupus erythematosis, and Sjogren's syndrome, and less frequently in rheumatoid arthritis (33). There is good evidence that these autoantibodies play a direct pathogenic role in neonatal lupus erythematosis and subacute cutaneous lupus erythematosis (33, 34). However, the mechanism by which the immune system initially responds to Ro/SSA and other intracellular self-antigens is not clear. One popular hypothesis suggests that molecular mimicry is an important initiating mechanism, i.e., aspects of the immune response to a microbe cross react with self-proteins (35). Conceivably, overexpression of a commonly targeted autoantigen, such as the Ro/SSA antigen in HCMV-infected cells, also could favor an autoimmune response. Although the Ro/SSA 52 kDa antigen is normally found in the nucleus and cytoplasm, it can be detected on the surface of peripheral lymphocytes that have been stressed by heat shock or treatment with ultraviolet light (36). Perhaps stress induced by HCMV infection also leads to cell surface presentation of Ro/SSA, facilitating an autoimmune response to the overexpressed antigen. Murine cytomegalovirus has been shown to induce autoimmune antibodies in infected mice (37–40), although Ro/SSA antibodies were not monitored in these studies.

Lipocortin 1, cPLA2 and COX-2 mRNAs. Multiple constituents of the pathway that produces prostaglandin E2 from arachidonic acid are modulated by HCMV (Table 1). Cytosolic phospholipase A2 (cPLA2) mRNA increases by a factor of 12 and cyclooxygenase-2 (COX-2) mRNA is elevated by a factor of 7 at 24 h after infection. Lipocortin 1, also known as annexin I, mRNA decreases by a factor of 9 at 24 h after infection. When cPLA2 is activated by phosphorylation, it translocates to membranes where it selectively cleaves and releases arachidonic acid; then COX2 converts it to prostaglandin E2. Lipocortin 1 inhibits the activation of cPLA2 (41). Thus, in HCMV-infected fibroblasts, the synthesis of prostaglandin E2 is activated by the induction of cPLA2 and COX2 and the inhibition of the negative regulator lipocortin 1, assuming that the changes in mRNA levels translate to changes in active proteins. Further, HCMV infection has been shown to activate latent cPLA2 by inducing its phosphorylation (42). Thus, this pathway is strongly induced at both the transcriptional and posttranslational levels after infection, and this should lead to a marked increase in the production of prostaglandin E2. Prostaglandins serve as second messengers to stimulate a variety of responses, including inflammation. Perhaps the activation of this pathway is a cellular reaction to HCMV infection designed to induce a cell-mediated response that will kill the infected cell and thereby inhibit spread of the infection. Alternatively, one might speculate that the virus either induces the pathway or fails to antagonize the induction as a strategy to facilitate spread of the virus within the infected host. Inflammation might serve to lure monocytes and monocytic precursors to the vicinity of the infected cells where they can be infected. Cells of the monocytic lineage harbor HCMV on a long-term basis in a latent state (43–45).

It is possible that the concerted changes in cPLA2, COX-2 and lipocortin 1 are an indirect effect of HCMV gene action. IL-1β has been shown to regulate this set of genes (46) in the same manner as seen in infected cells. Although several reports have suggested that IL-1β activity is decreased in cultures of HCMV-infected monocytes (47, 48), the HCMV IE1 gene has been shown to induce the accumulation of IL-1β mRNA in transfected monocytes (49, 50). The IL-1β gene was not included in the oligonucleotide arrays assayed in this report, so we do not know if its mRNA is induced by infection of fibroblasts.

Thombospondin-1 mRNA. Thombospondin-1 is a calcium-binding protein released upon platelet activation (51). It is a constituent of the extracellular matrix that regulates cell growth and differentiation, and it might potentiate tumor progression (52). Recently, thombospondin-1-deficient mice have been produced (53) whose lungs exhibit acute and chonic cell infiltrates with increased fibroblastic and epithelial cell proliferation, matrix deposition and diffuse alveolar hemorrhage characteristic of pneumonia. HCMV causes a 21-fold reduction in the level of thombospondin-1 mRNA by 24 h after infection (Table 1). Replication in the lung that leads to pneumonia is one of the principle consequences of active HCMV infection in immunosuppressed individuals (54). Given the phenotype of thombospondin 1-deficient mice, one can speculate that the reduction in this mRNA might contribute to pneumonia induced by acute HCMV infection.

MITF mRNA. The microphthalmia-associated transcription factor (MITF) is the product of the microphthalmia gene. Mice have been described with a variety of mutations in this gene (55), and the most severe manifestations of the mutations include microphthalmia, oeteopetrosis and deafness. In the human, MITF mutations were identified in two families afflicted with Waardenberg syndrome type 2, which causes hearing loss and patchy pigmentation of the eyes, hair and skin (56). Infection of humans with HCMV early in pregnancy has been reported to cause anophthalmia (57) and congenital infection of mice with murine cytomegalovirus can cause microphthalmia (58). Modulation of MITF mRNA levels by the virus could contribute to these abnormalities. MITF mRNA is reduced by a factor of 4–8 at 24 h after HCMV infection of fibroblasts. Whereas the association of HCMV with eye abnormalities appears to be rare, congenital HCMV infection is a common cause of hearing loss. Conceivably, HCMV-induced hearing loss is a consequence of an inhibitory effect on MITF mRNA expression during development. This supposition is consistent with the observation that MITF mutations are associated with hearing loss in the Waardenberg syndrome. HCMV could potentially modulate MITF in cells that are eventually killed or in cells where viral gene expression does not lead to cell death.

Conclusion. The roles of the cellular genes discussed above in HCMV replication and pathogenesis remain highly speculative. Nevertheless, the ability to identify cellular genes whose functions provide tantalizing hints of potential mechanistic roles in infectious disease processes underscores the utility of gene array technology in the study of pathogens. The global analysis of changes in mRNA levels provides a catalog of genes that are modulated as a result of the host-pathogen interaction and therefore deserve further scrutiny. DNA array analysis provides an important new approach for the investigation of pathogenic mechanisms.

REFERENCES

1. Yurochko, A. D., Hwang, E. S., Rasmussen, L., Keay, S., Pereira, L. & Huang, E. S. (1997) *J. Virol.* 71, 5051–5059.
2. Liu, B. & Stinski, M. F. (1992) *J. Virol.* 66, 4434–4444.
3. Pizzorno, M. C., O'Hare, P., Sha, L., LaFemina, R. L. & Hayward, G. S. (1988) *J. Virol.* 62, 1167–1179.
4. Malone, C. L., Vesole, D. H. & Stinski, M. F. (1990) *J. Virol.* 64, 1498–1506.
5. Stenberg, R. M., Fortney, J., Barlow, S. W., Magrane, B. P., Nelson, J. A. & Ghazal, P. (1990) *J. Virol.* 64, 1556–1565.
6. Chee, M. S., Satchwell, S. C., Preddie, E., Weston, K. M. & Barrell, B. G. (1990) *Nature* 344, 774–777.
7. Welch, A. R., McGregor, L. M. & Gibson, W. (1991) *J. Virol.* 65, 3915–3918.
8. Jault, F. M., Jault, J. M., Ruchti, R., Fortunato, E. A., Clark, C., Corbeil, J., Richman, D. D. & Spector, D. H. (1995) *J. Virol.* 69, 6697–6704.
9. Bresnahan, W. A., Boldogh, I., Thompson, E. A., & Albrecht, T. (1996) *Virology* 224, 150–160.
10. Lu, M. & Shenk, T. (1996) *J. Virol.* 70, 8850–8857.
11. Dittmer, D. & Mocarski, E. S. (1997) *J. Virol.* 71, 1629–1634.
12. Mocarski, E. S. (1996) in *Fields Virology,* eds. Fields, B. N., Knipe, D. M. & Howley, P. M. (Lippencott, Philadelphia), $3^{rd}$ Ed., pp. 2447–2492.
13. Zhu, H., Cong, J-P. & Shenk, T. (1997) *Proc. Natl. Acad. Sci. USA* 94, 13985–13990.
14. Baldick, C. J. & Shenk, T. (1996) *J. Virol.* 70, 6097–6105.
15. Wodicka, L., Dong, H., Mittmann, M., Ho, M. & Lockhart, D. J. (1997) *Nature Biotech.* 15, 1359–1367.
16. Lockhart, D. J., Dong, H., Byrne, M. C., Follette, M. T., Gallo, M. V., Chee, M. S., Mittmann, M., Wang, C., Kobayashi, M., Horton, H. & Brown, E. L. (1996) *Nature Biotech.* 14, 1675–1680.
17. Fodor, S. P. A., Read, J. L., Pirrung, M. C., Stryer, L., Lu, A. T. & Solas, D. (1991) *Science* 251, 767–773.
18. Fodor, S. P. A., Rava, R. P., Huang, X. C., Pease, A. C., Holmes, C. P. & Adams, C. L. (1993) *Science* 364, 555–556.
19. Pease, A. C., Solas, D., Sullivan, E. J., Cronin, M. T., Holmes, C. P. & Fodor, S. P. A. (1994) *Proc. Natl. Acad. Sci. USA* 91, 5022–5026.
20. Lipshutz, R. J., Morris, D., Chee, M., Hubbell, E., Kozal, N. S., Shen, N., et al. (1995) *BioTechniques* 19, 442–447.
21. Chee, M., Yang, R., Hubbell, E., Berno, A., Huang, X. C., Stern, D., Winkler, J., Lockhart, D. J., Morris, M. S. & Fodor, S. P. A. (1996) *Science* 274, 610–614.

22. Quinnan, G. V., Jr., Delery, M., Rook, A. H., Frederick, W. R., Epstein, J. S., Manischewitz, J. F., Jackson, L., Ramsey, K. M., Mittal, K., Plotkin, S. A., et al. (1984) *Ann. Intern. Med.* 101, 478–483.
23. Ahn, K., Angulo, A., Ghazal, P., Peterson, P. A., Yang, Y. & Fruh, K. (1996) *Proc. Natl. Acad. Sci. USA* 93, 10990–10995.
24. Jones, T. R., Wiertz, E. J., Sun, L., Fish, K. N., Nelson, J. A. & Ploegh, H. L. (1996) *Proc. Natl. Acad. Sci. USA* 93, 11327–11333.
25. Wiertz, E. J., Jones, T. R., Sun, L., Bogyo, M., Geuze, H. J. & Ploegh, H. L. (1996) *Cell* 84, 769–779.
26. Ahn, K., Gruhler, A., Galocha, B., Jones, T. R., Wiertz, E. J., Ploegh, H. L., Peterson, P. A., Yang, Y. & Fruh, K. (1997) *Immunity* 6, 613–621.
27. Hengel, H., Koopmann, J. O., Floh, T., Muranyi, W., Goulmy, E., Hammerling, G. J., Koszinowski, U. H. & Momburg, F. (1997) *Immunity* 6, 623–632.
28. Jones, T. R. & Sun, L. (1997) *J. Virol.* 71, 2970–2979.
29. Braud, V., Jones, E. Y. & McMichael, A. (1997) *Eur. J. Immunol.* 27, 1164–1169.
30. Borrego, F., Ulbrecht, M., Weiss, E. H., Coligan, J. E. & Brooks, A. G. (1998) *J. Exp. Med.* 187, 813–818.
31. Braud, V. M., Allan, D. S. J., O'Callaghan, C. A., Soderstrom, K., D'Andrea, A., Ogg, G. S., Lazetic, S., Yound, N. T., Bell, J. I., Phillips, J. H., Lanier, L. L. & McMichael, A. J. (1998) *Nature* 391, 795–799.
32. Rayburn, H. T., Mandelboim, O., Vales-Gomez, M., Davis, D. M., Pazmany, L. & Strominger, J. L. (1997) *Nature* 386, 514–517.
33. Bouffard, P., Laniel, M-A. & Boire, G. (1996) *J. Rheumatol.* 23, 1838–1841.
34. Finkelstein, Y., Adler, Y., Harel, L., Nussinovitch, M. & Youinou, P. (1997) *Ann. Med. Interne (Paris)* 148, 205–208.
35. Herrath, M. G. & Oldstone, M. B. A. (1996) *Curr. Opin. Immunol.* 8, 878–885.
36. Igarashi, T., Itoh, Y., Fukunaga, Y. & Yamamoto, M. (1995) *Autoimmunity* 22, 33–42.
37. O'Donoghue, H. L., Lawson, C. M. & Reed, W. D. (1990) *Immunol.* 71, 20–28.
38. Lawson, C. M., O'Donoghue, H. L., Farrell, H. E., Shellam, G. R., and Reed, W. D. (1991) *Immunol.* 72, 426–433.
39. Price, P., Olver, S. D., Gibbons, A. E. & Shellam, G. R. (1993) *Immunol.* 78, 14–21.
40. Chapman, A. J., Farrell, H. E., Thomas, J. A., Papadimitriou, J. M., Garlepp, M. J., Scalzo, A. A. & Shellam, G. R. (1994) *Immunol.* 81, 435–443.
41. Croxtall, J. D., Choudhury, Q., Newman, S. & Flower, R. J. (1996) *Biochem. Pharmacol.* 52, 351–356.
42. Shibutani, T., Johnson, T. M., Yu, Z. X., Ferrans, V. J., Moss, J. & Epstein, S. E. (1997) *J. Clin. Invest.* 100, 2054–2061.
43. Kondo, K., Xu, J. & Mocarski, E. S. (1996) *Proc. Natl. Acad. Sci. USA* 93, 11137–11142.
44. Sinclair, J. & Sissons, P. (1996) *Intervirol.* 39, 293–301.
45. Soderberg-Naucler, C., Fish, K. N. & Nelson, J. A. (1997) *Cell* 91, 119–126.
46. Croxtall, J. D., Newman, S. P., Choudhury, Q. & Flower, R. J. (1996) *Biochem. Biophys. Res. Commun.* 220, 491–495.
47. Rogers, B. C., Scott, D. M., Mundin, J. & Sissons, J. G. P. (1985) *J. Virol.* 55, 527–532. 49. Iwamoto, G. K., Monick, M. M., Clark, B. D., Auron, P. E., Stinski, M. F. & Hunninghake, G. W. (1990) *J. Clin. Invest.* 85, 1853–1857.
48. Kapasi, K. & Rice, G. P. A. (1998) *J. Virol.* 62, 3603–3607.
49. Iwamoto, G. K., Monick, M. M., Clark, B. D., Auron, P. E., Stinski, M. F. & Hunninghake, G. W. (1990) *J. Clin. Invest.* 85, 1853–1857.
50. Crump, J. W., Geist, L. J., Auron, P. E., Webb, A. C., Stinski, M. F. & Hunninghake, G. W. (1992) *Am. J. Respir. Cell. Mol. Biol.* 6, 674–677.
51. Adams, J. C. (1997) *Int. J. Biochem. Cell Biol.* 29, 861–865.
52. Tuszynski, G. P. & Nicosia, R. F. (1995) *BioEssays* 18, 71–76.
53. Lawler, J., Sunday, M., Thibert, V., Duquette, M., George, E. L., Rayburn, H. & Hynes, R. O. (1998) *J. Clin. Invest.* 101, 982–992.
54. Britt, W. J. & Alford, C. A. (1996) in *Fields Virology*, eds. Fields, B. N., Knipe, D. M. & Howley, P. M. (Lippencott, Philadelphia), 3$^{rd}$ Ed., pp. 2493–2523.
55. Steingrimsson, E., Moore, K. J., Lamoreux, M. L., Ferre-D'Amare, A. R., Burley, S. K., Zimring, D. C. S., Skow, L. C., Hodgkinson, C. A., Arnheiter, H., Copeland, N. G. & Jenkins, N. A. (1994) *Nature Gen.* 8, 256–263.
56. Tassabehji, M., Newton, V. E. & Read, A. P. (1994) *Nature Genet.* 8, 251–255.
57. McCarthy, R. W., Frenkel, L. D., Kollarits, C. R. & Keys, M. P. (1980) *Am. J. Ophthalmol.* 90, 558–561.
58. Tsutsui, Y., Kashiwai, A., Kawamura, N. & Kadota, C. (1993) *Am. J. Pathol.* 143, 804–813.

The present invention provides greatly improved methods, compositions, and apparatus for identifying gene function and for studying the regulatory relationship among genes. It is to be understood that the above description is intended to be illustrative and not restrictive. Many variations of the invention will be apparent to those of skill in the art upon reviewing the above description. By way of example, the invention has been described primarily with reference to the use of a high density oligonucleotide array, but it will be readily recognized by those of skill in the art that other nucleic acid arrays, other methods of measuring transcript levels and gene expression monitoring at the protein level could be used. The scope of the invention should, therefore, be determined not with reference to the above description, but should instead be determined with reference to the appended claims, along with the full scope of equivalents to which such claims are entitled.

TABLE 1 mRNAs that increase or decrease ≥ 4-fold after HCMV infection

| | Actin/Tubulin/Myosin | | | | | Kinase/Phosphatase | | | |
|---|---|---|---|---|---|---|---|---|---|
| X06956 | alpha-tubulin | 24 h, 6 X | U | 3 | R39857 | est = X97630 - serine/threonine protein kinase EMK | 24 h, 4 X | U | 3 |
| R59199 | est = X79535 - beta tubulin | 24 h, 4 X | D | 3 | H02889 | est = Y11366 IMPA gene | 24 h, 8 X | U | 3 |
| Z24727 | tropomyosin isoform | 24 h, 4 X | D | 3 | U25994 | cell death protein (RIP protein kinase) | 8 h, 4 X | U | 1 |
| T92451 | est = M12125 - tropomyosin TM30 (pl) | 24 h, 5 X | D | 3 | D21209 | protein tyrosine phosphatase (PTP-BAS, type 1) | 8 h, 24 h, 4–6 X | D | 1 |
| X05276 | fibroblast tropomyosin TM30 (pl) | 24 h, 4 X | D | 3 | X77278 | HYL tyrosine kinase | 24 h, 8 X | D | 3 |
| T60155 | est = 305192 - alpha-actin (ACTA) | 24 h, 11 X | D | 3 | R60908 | est = X74764 - receptor protein tyrosine kinase | 24 h, 21 X | D | 1 |
| M19283 | gamma-actin | 24 h, 4 X | D | 3 | H65441 | est = U78027, L35265 - Bruton's tyrosine kinase | 24 h, 7 X | D | 3 |
| X54163 | cardiac troponin I | 24 h, 5 X | D | 3 | X16416 | proto-oncogene tyrosine-protein kinase (abl) | 24 h, 4 X | D | 1 |
| H44011 | myosin heavy chain | 8 h, 5 X | D | 3 | | Lamins | | | |
| T55741 | est = X85337 - myosin light chain kinase (MLCK) | 24 h, 6 X, | D | 3 | M55210 | laminin BZ chain | 24 h, 4–8 X | D | 3 |
| X53416 | actin-binding protein (filamin) (ABP-280) | 24 h, 5 X | D | 1 | X79683 | bata laminin | 24 h, 4–5 X | D | 3 |
| T97948 | neutal calponin | 24 h, 15 X | D | 3 | R43734 | S78569 - laminin alpha 4 chain | 24 h, 6 X | D | 3 |
| | Cell Cycle | | | | T55218 | est = M13452 or M13451 - lamin A or C | 8 h, 26 X | D | 3 |
| L49231 | retinoblastoma susceptibility protein (RBI) | 24 h, 12 X | U | 3 | | Ligands and Receptors | | | |
| X59798 | PRADI mRNA for cyclin | 24 h, 9 X | D | 3 | L13740 | TR3 orphan receptor | 8, 24 h, 6–46 X | D | 1 |
| D13891 | Id-2H | 8 h, 24 h, 6–7 X | D | 3 | U12767 | mitogen induced nuclear orphan receoptor | 8 h, 5 X | U | 3 |
| L13698 | gas-1 (growth-arrest-specfic gene) | 8 h, 24, 6–15 X | D | 1 | M77140 | pro-galanin | 24 h, 20 X | U | 1 |
| X62048 | Woel hu | 8 h, 24 h, 4–5 X | D | 3 | M63888 | heparin-binding growth factor receptor | 24 h, 9 X | U | 3 |
| H50438 | est = M81934 - cdc23B | 8 h, 4 X | D | 3 | T70920 | est = M88279 - Immunophilin FKBP52 | 24 h, 8 X | U | 3 |
| U09477 | 53BPI p53-binding protein | 8 h, 5 X | D | 3 | M20132 | androgen receptor (AR) | 8 h, 4 X | D | 3 |
| | Coagulation | | | | M19481 | follistatin | 24 h, 6–15 X | D | 1 |
| R16659 | est = L27624 and AC002076 - TFPI-2 | 24 h, 8 X | U | 1 | T71662 | est = M14118 - Insulin-like growth factor (IGF-II) | 24 h, 4 X | D | 1 |
| M59499 | lipoprotein-associated coagulation inhibitor | 8 h, 6 X | D | 3 | M35878 | Insulin-like growth factor-binding protein-3 | 24 h, 4 X | D | 3 |
| M14083 | beta-migrating plasminogen activator inhibitor 1 | 24 h, 4 X | D | 3 | M65062 | Insulin-like growth factor-binding protein-5 | 8 h, 24 h, 4–12 X | D | 3 |
| J02933 | blood coagulation factor VII gene | 8 h, 5 X | D | 3 | M35410 | Insulin-like growth factor binding protein 2 | 40', 8 h, 5–11 X | D | 3 |
| | Complement | | | | X04434 | Insulin-like growth factor 1 receptor. | 40', 8 h, 24 h, 4 X | D | 3 |
| M31516 | decay-accelerating factor (DAF) | 8 h, 24 h, 4–5 X | U | 1 | L07594 | transforming growth factor-beta type III receptor | 8 h, 24 h, 4–6 X | D | 1 |
| T54547 | est = M84526 - adipsin/complement factor D | 24 h, 7 X | D | 3 | M21574 | platelet-derived growth factor receptor alpha | 8 h, 24 h, 12–25 X | D | 1 |
| T69603 | est = M14058 - complement clr component | 24 h, 4 X | D | 3 | H88938 | est = M60828 M25295 - keratinocyte growth factor | 8 h, 4 X | D | 3 |
| R12676 | est = M65292 - 1.4-kb mRNA of complement factor H | 40', 4 X | D | 3 | X62381 | activin receptor; growth factor-like receptor | 8 h, 6 X | D | 3 |
| | Cytokines/Receptors | | | | R45296 | est = U67384 - orphan G protein-coupled receptor | 24 h, 6 X | D | 3 |
| M21121 | rantes | 8 h, 6 X | U | 2 | X02157 | fetal erythropoietin | 24 h, 4 X | D | 3 |
| M29150 | Interleulin 6 | 8 h, 10 X | U | 3 | M64497 | apolioprotein A1 regulatory protein (ARP-1) | 8 h, 4–5 X | D | 3 |
| X58377 | interleukin-11 (IL-11) | 8, 24 h, 4–11 X | U | 3 | L11708 | 17 beta hydroxysteroid dehydrogenase type 2 | 24 h, 7 X | D | 3 |
| M29696 | interleulin-7 (IL-7) receptor, alpha chain | 24 h, 4 X | U | 1 | L00352 | low density lipoprotein (LDL) receptor | 8 h, 24 h, 5–6 X | D | 3 |
| U02020 | pre-B cell enhancing factor (PBEF) | 8 h, 24 h, 4 X | U | 3 | M10065 | apolioprotein E | 40', 8 h, 7–26 X | D | 3 |
| T61446 | A20 | 8 h, 4 X | U | 3 | | Prostaglandin Synthesis | | | |
| L35263 | CSaids binding protein (CSBPI) | 8 h, 7 X | D | 3 | U04636 | cyclooxygenase-2 (cox2) | 8 h, 7 X | U | 3 |
| M58286 | tumor necrosis factor receptor | 8 h, 24 h, 4–5 X | D | 1 | M72393 | cytosolic phospholipase A2 (cPLA2) | 8 h, 24 h, 7–12 X | U | 3 |
| H14506 | est = L36034 - pre-B cell stimulating factor | 24 h, 4 X | D | 1 | X05908 | lipocortin | 24 h, 9 X | D | 3 |

TABLE 1-continued mRNAs that increase o rease ≧ 4-fold after HCMV infection

| | | | | | | | | | |
|---|---|---|---|---|---|---|---|---|---|
| X72012 | endoglin | 8 h, 23 X | D | 3 | D38143 | prostacyclin synthase | | 24 h, 4 X | D |

Extracellular Matrix and Cell Adhesion | | Protein Degradation

| | | | | | | | | | |
|---|---|---|---|---|---|---|---|---|---|
| L36531 | integrin alpha 8 subunit | 40', 6 X | U | 3 | T56244 | est = D26599 - proteasome subunit HsC7-I | | 24 h, 6 X | U |
| M80244 | E16, an integral membrane protein | 40', 4 X | U | 3 | T54276 | proteasome subunit LMP7 (allele LMP7C) | | 8 h, 4 X | U |
| X14787 | thrombospondin 1 (TSP1) | 24 h, 21 X | D | 1 | T92259 | proteasome component IOTA chain | | 24 h, 5 X | D |
| L12350 | thrombospondin 2 (TSP2) | 24 h, 13 X | D | 3 | D00762 | proteasome component HC8 | | 24 h, 6 X | D |
| X05231 | collagenase | 40', 8 h, 4–7 X | D | 3 | D00760 | proteasome component C3 | | 24 h, 5 X | D |
| L25285 | collagen alpha-1 type XV (COL15A1) | 24 h, 13 X | D | 3 | H05893 | 26S proteasome subunit p97 | | 24 h, 4 X | D |
| J03464 | collagen alpha-2 type I | 24 h, 14 X | D | 3 | L02426 | 26S protease (S4) regulatory subunit | | 24 h, 16 X | D |
| M11718 | collagen alpha-2 type V | 24 h, 8 X | D | 3 | M91670 | ubiquitin carrier protein (E2-EPF) | | 24 h, 4 X | D |
| M34570 | collagen alpha-2 type VI | 24 h, 6 X | D | 3 | R67921 | est = D55696 - putative cysteine protease | | 8 h, 4 X | D |
| T51558 | est = K01228 - procollagen alpha 1(I) chain | 24 h, 6 X | D | 3 | T56256 | est = U20657 - ubiquitin protease proto-oncogene | | 8 h, 4 X | D |
| X06700 | pro-alpha(III) collagen | 24 h, 16 X | D | 1 | J03589 | ubiquitin-like protein (GdX) | | 24 h, 7 X | D |
| L16895 | lysyl oxidase, an extracellular copper enzyme | 24 h, 4 X | D | 3 | T50500 | est = Z22658 - a placental thrombia inhibitor (PTI) | | 24 h, 4 X | D |
| X53743 | fibulin-1 C - a secreted glycoprotein | 40', 8, 24 h, 5–7 X | D | 3 | | | Proto-oncogenes | | |
| U34976 | gamma-sarcoglycan, a dystrophin-associated protein | 24 h, 6 X | D | 3 | X89985 | BCL7B gene | | 8 h, 24 h, 5–10 X | U |
| U14394 | tissue inhibitor of metalloproteinase-3 (TIMP3) | 24 h, 6–8 X | D | 3 | H48122 | est = U43746, breast cancer susceptibility (BRCA2) | | 8 h, 4 X | U |
| R32771 | est = U37791 - rasi-1 matrix metalloproteinase | 8 h, 24 h, 5–9 X | D | 3 | M83751 | arginine-rich protein ARP | | 24 h, 11 X | U |
| U03877 | extracellular protein (SI-5) | 24 h, 4 X | D | 3 | M27903 | pim-1 proto-oncogene | | 24 h, 16 X | U |
| L34056 | cadherin-11 | 24 h, 9 X | D | 3 | T53138 | est = Y11306 - hTCF-4 | | 8 h, 4 X | D |

GTP Binding Proteins | | | | | X16416 | proto-oncogene tyrosine-protein kinase (abl) | | 24 h, 4 X | D |

| | | | | | | | | | |
|---|---|---|---|---|---|---|---|---|---|
| H67367 | est ew D38076 - RanBP1 (Ran-binding protein 1) | 24 h, 3 X | D | 3 | D43969 | AMLlc protein | | 8 h, 24 h, 4 X | D |
| T93295 | est:homo. of L20294-mouse GTP-binding protein | 24 h, 4 X | U | 3 | X82209 | MN1 | | 8 h, 24 h, 4–7 X | D |
| X75593 | rab 13 | 24 h, 9 X | D | 3 | | | Splicing Factors | | |
| R53966 | est = Z22641 - a2-chimaerin | 8 h, 8 X | D | 3 | X13482 | U2 small nuclear ribonucleoprotein A' | | 24 h, 4 X | U |
| H19201 | est: homo to mouse L07924 - gua. nucl. disso. stim. | 8 h, 9 X | D | 3 | M15841 | U2 small nuclear RNA-associated B" | | 8 h, 4 X | U |

Heat Shock and Stess-Inducible Proteins | | | | | R41349 | splicing factor, arginine/serine-rich 7 (SFR57) | | 24 h, 10 X | U |

| | | | | | | Transcription Factors | | | |
|---|---|---|---|---|---|---|---|---|---|
| R08183 | est = X75821, U07550 - chaperonin 10 | 24 h, 8 X | U | 3 | R55041 | est = J03161 - serum response factor (SRF) | | 24 h, 5 X | U |
| T66307 | heat shock 7-kDa protein I | 24 h, 11 X | D | 3 | H46624 | est: homology to mouse AB012276 - AITFx | | 8 h, 4 X | U |
| M86752 | transformation-sensitive protein | 24 h, 8 X | D | 3 | M97676 | homeobox protein (HOX7) | | 8 h, 4 X | U |
| L08069 | heat shock protein, E. coli DnaJ homologue | 8 h, 24 h, 6–15 X | D | 3 | R26139 | est = X59268 - TFIIB | | 8 h, 8 X | U |
| H55758 | est = M14328 alpha enolase | 8 h, 4 X | D | 3 | M69043 | MAD-3, encodes an I kappa B-like protein | | 8 h, 24 h, 6–10 X | U |
| T93272 | est = M62829 early growth response protein I | 8, 24 h, 5–6 X | D | 1 | R26146 | NF-kB p105 subunit | | 24 h, 4 X | U |
| T51856 | est: homo, so stress-inducible chaperone mt-GrpE#1 | 24 h, 4 X | D | 3 | U09825 | acid finger protein (AFP) | | 8 h, 24 h, 5–8 X | U |
| X79066 | ERF-1 | 8 h, 4 X | D | 3 | H88261 | est = U90304 iroquois-class homeodomain protein | | 8 h, 4 X | U |

Interferon | | | | | X03348 | beta-glucocorticoid receptor | | 8 h, 24 h, 4 X | D |

| | | | | | | | | | |
|---|---|---|---|---|---|---|---|---|---|
| M24594 | Interferon stimulated genes 54K (isg54K) | 8 h, 24 h, 5–19 X | U | 2 | M83667 | NF-IL6-beta protein | | 8 h, 24 , 4–6 X | D |
| M87434 | 71 kDa 2'5' oligoadenylate synthetase | 8 h, 6 X | U | 2 | X57435 | transcription factor AP-4 | | 8 h, 24 h, 4 X | D |
| X02875 | (2'–5') oligo A synthetase E (1.8 kb RNA) | 8 h, 24 h, 6–15 X | U | 2 | M36711 | sequence-specific DNA-binding protein (AP-2) | | 8 h, 6 X | D |
| X02874 | (2'–5') oligo A synthetase E (1.6 kb RNA) | 8 h, 8 X | U | 2 | Y00345 | poly A binding protein | | 24 h, 5 X | D |
| M87284 | 69 kDa 2'5' oligoadenylate synthetase | 8 h, 8 X | U | 2 | R39209 | est = X65644 - MBP-2 for MHC binding protein 2 | | 24 h, 5 X | D |
| X02530 | gamma-Interferon inducible early response gene | 8 h, h, 34 X | U | 1 | L19872 | aryl hydrocarbon receptor (AhR) | | 8 h, 24 h, 4–8 X | D |
| L05072 | interferon regulatory factor 1 (IRF-1) | 24 h, 7 X | U | 2 | | | | | |

TABLE 1-continued mRNAs that increase o rease ≧ 4-fold after HCMV infection

| | | 8 h, 5–12 X | U | 2 | | Translation Factors | |
|---|---|---|---|---|---|---|---|
| X15949 | interferon regulatory factor-2 (IRF-2) | | | | R72300 | est = U17969 - translation initiation factor eIF-5A | 24 h, 149 X | U |
| X67325 | Interferon-alpha inducible gene; p27 gene | 24 h, 7–28 X | U | 2 | H04333 | est = U49436 - translation initiation factor 5 (eIF5) | 24 h, 36 X | U |
| H05300 | interferon-induced guanylate-binding protein 1 | 8 h, 24 h, 9–27 X | U | 2 | T69446 | est = D13748 initiation factor 4A-1 (eIF-4A1) | 24 h, 39 X | U |
| M55542 | guanylate binding protein insoform II | 8 h, 9 X | U | 2 | L18960 | translation initiation factor (eIF-4C) | 24 h 39 X | U |
| D31887 | KIAA0062 (cig19) | 8 h, 24 h, 3–4 X | U | 2 | H01943 | eukaryotic initiation factor 4E (eIF-4E) | 24 h, 4 X | U |
| X82200 | interferon inducible gene staf50 | 24 h, 14 X | U | 1 | X62570 | IFP53, tryptophanyl-tRNA synthetase | 8 h, 24 h, 6–800 X | U |
| X02492 | interferon-induced protein 6-16 | 8 h, 24 h, 4–5 X | U | 2 | M81592 | gammma-glutamyl carboxylase (hGC) | 24 h, 5 X | U |
| R34698 | interferon-inducible protein 9-27 | 8 h, 24 h, 3–6 X | U | 2 | Z12630 | SSR (signal-sequence receptor) alpha subunit | 24 h, 5 X | U |
| M13755 | interferon-induced 17-kDa/15-kDa protein | 8, 24 h, 55–260 X | U | 2 | R60357 | alanyl tRNA synthetase | 8 h, 5 X | D |
| M28622 | interferon beta | 8 h, 24 h, 10–31 X | U | 2 | D31762 | KIAA0057 gene - homolog of TRAMP | 24, 8 X | D |
| X17668 | indoleamine 2,3-dioxygenase | 8 h, 24 h, 9–140 X | U | 1 | | Miscellaneous | | |
| M33882 | MxA | 8 h, 24 h, 5–118 X | U | 2 | | | | |
| M30818 | MxB | 8 h, 24 h, 23–53 X | U | 2 | M34551 | 52 k autoantigen in Ro/SSA ribonucleoprotein compl. | 8 h, 24 h, 4–12 X | U |
| X56841 | HLA-E gene | 8 h, 24 h, 5–19 X | U | 1 | U33286 | chromosome segregation gene homolog CAS | 24 h, 4 X | U |
| T50250 | est: homo. to U51904, mouse IFN α-treated mRNA | 24 h, 32 X | U | 2 | T88721 | est = U52100, X94770 - XMP mRNA | 24 h, 4 X | U |
| M60618 | nuclear autoantigen Sp100 | 8 h, 24 h, 4–16 X | U | 2 | M26697 | nucleolar phosphoprotein B23 | 24 h, 12 X | U |
| M73778 | PML-1 | 8 h, 24 h, 3–6 X | U | 1 | J05682 | subunit C of V-ATPase (vat C) | 24 h, 8 X | U |
| M22349 | neuron-specific gamma-2 enolase | 8 h, 24 h, 4–14 X | U | 3 | | | | |
| M24470 | glucose-6-phosphate dehydrogenase | 24 h, 8 X | U | 3 | | | | |
| T43964 | purine nucleoside phosphorylase | 24 h, 9 X | U | 3 | | | | |
| U07681 | NAD(H)-specific isocitrate dehydrogenase α subunit | 24 h, 6 X | U | 1 | | | | |
| R42235 | est = X56452 - CYP2C gene for cytochrome P450 | 24 h, 6 X | U | 3 | | | | |
| H53120 | est = D12676 - lysosomal sialoglycoprotein | 24 h, 8 X | U | 3 | | | | |
| J00123 | enkephalin gene | 24 h, 20 X | U | 3 | | | | |
| H28131 | est = M64784 - platelet 6-phosphofructokinase | 24 h, 6 X | U | 3 | | | | |
| R42244 | est = X57522 - antigen peptide transporter 1 | 24 h, 6 X | U | 3 | | | | |
| R26294 | est = AP017732 - chromosome 2 cosmids | 24 h, 4 X | U | 3 | | | | |
| L25270 | XE169 | 24 h, 5 X | U | 3 | | | | |
| U01833 | a putative nucleotide-binding protein | 8 h, 24 h, 6–7 X | U | 1 | | | | |
| H72850 | est = X56351 5 - aminolevulinate synthase | 24 h, 7 X | D | 3 | | | | |
| U29195 | neuronal pentraxin II (NPTX2) | 8 h, 24 h, 4 X | D | 3 | | | | |
| U19523 | GTP cyclohydrolase I | 24 h, 7 X | D | 3 | | | | |
| H03980 | est = AB001106 - glia maturation factor | 24 h, 5 X | D | 3 | | | | |
| L19779 | histone H2A.2 | 8 h, 24 h, 4–8 X | D | 3 | | | | |
| Z29678 | mitF | 24 h, 4–8 X | D | 1 | | | | |
| X69978 | ERCC5 excision repair protein | 8 h, 5 X | D | 3 | | | | |
| X65024 | xeroderma pigmentosum group C compl. factor | 24 h, 4 X | D | 3 | | | | |
| R60318 | est = AF022813 - tetraspan (NAG-2) | 24 h, 28 X | D | 3 | | | | |
| H87106 | est = AF043906 - T245 protein (T245) | 24 h, 4 X | D | 3 | | | | |
| U14650 | platelet-endothelial tetraspan antigen 3 | 24 h, 23 X | D | 3 | | | | |
| L13385 | Miller-Dieker lissencephaly protein (LISI) | 24 h, 4 X | D | 3 | | | | |
| L35263 | CSaids binding protein (CSBPI) | 8 h, 7X | D | 3 | | | | |
| D10522 | 80K-L protein - a major substrate for protein kinase C | 8 h, 24 h, 4–8 X | D | 1 | | | | |
| J02814 | chondroitin sulfate proteoglycan core protein | 24 h, 26 X | D | 3 | | | | |
| X75090 | HLA-DR associated protein I (PHAPI) | 8 h, 4–8 X | D | 3 | | | | |
| U08092 | histamine N-methyltransferase (HNMT) | 8h, 4 X | D | 3 | | | | |
| D14874 | adrenomedullin | 8 h, 24 h, 14–18 X | D | 1 | | | | |
| H80262 | est = X15422 - mannose-binding protein C | 24 h, 8 X | D | 3 | | | | |

TABLE 1-continued mRNAs that increase or rease ≥ 4-fold after HCMV infection

| | | | | |
|---|---|---|---|---|
| R88575 | est = U55017 M86521 - transketolase (TKT) | 24 h, 5 X | D | 1 |
| M13994 | sytosolic aldehyde dehydrogenase (ALDHI) | 24 h, 5–7 X | D | 1 |
| M22324 | aminopeptidase N/CD13 mRNA | 24 h, 4 X | D | 3 |
| M12996 | glucose-6-phosphate dehydrogenase (G6PD) | 24 h, 5 X | D | 1 |
| T52343 | est = Y00433 - glutathione peroxidase | 24 h, 4 X | D | 3 |
| T64167 | est = dihydrodiol dehydrogenase isozyme DD2 | 8 h, 24 h, 4–21 X | D | 3 |
| X58022 | corticotropia-releasing factor binding protein | 24 h, 4 X | D | 3 |
| U03688 | dioxin-inducible cytochrome P450 (CYP1BI) | 8 h, 24 h, 4–11 X | D | 3 |
| H67764 | est = U55764 - estrogen sulfotransferase | 24 h, 5–12 X | D | 3 |
| D00137 | class I alcohol dehydrogenase beta-1 subunit | 8 h, 5 X | D | 3 |
| M77836 | pyrroline 5-carboxylate reductase (EC 1.5.1.2) | 24, 15 X | D | 3 |
| T57002 | est = M29038 - stem cell protein (SCL) | 24 h, 4 X | D | 3 |
| D13665 | est = D13665 - osteoblast specific factor 2 (OSF-2pl) | 24 h, 7 X | D | 3 |
| M22490 | bone morphogenetic protein-2B (BMP-2B) | 8 h, 4 X | D | 3 |
| M95787 | 22kDa smooth muscle protein (SM22) | 24 h, 5 X | D | 3 |
| Z11559 | iron regulatory factor (IRF) | 8 h, 24 h, 5 X | D | 3 |
| T63612 | ferritin heavy chain | 8 h, 4 X | D | 3 |
| T72863 | est = M10119 - ferritin light subunit | 24 h, 287 X | D | 3 |
| R56881 | est = U61166 - *Xenopus laevis* intersectin homolog | 8 h, 4–5 X | D | 3 |
| T63052 | est; homolog of *M. musculus* X52102 | 24 h, 5 X | U | 3 |
| D14663 | KIAA0107 gene | 24 h, 4 X | U | 3 |
| R61352 | est = D42085 KIAA0095 gene | 24 h, 6 X | U | 3 |
| U16954 | AFlq | 24 h, 5 . 7 X | U | 3 |
| R98335 | est = L13744 AF-9 (unknown function) | 8 h, 4–5 X | U | 3 |
| R01072 | est: unknown | 24 h, 10 X | U | 1 |
| R10664 | est: unknown | 24 h, 5–7 X | U | 3 |
| H24245 | est: unknown | 24 h, 4–5 X | U | 3 |
| H11036 | est: unknown | 24 h, 6 X | U | 3 |
| R42152 | est: unknown | 24 h, 7 X | U | 3 |
| R74454 | est: unknown | 8 h, 24 h, 4 X | U | 3 |
| R54359 | est: unknown | 24 h, 10 X | U | 3 |
| R01124 | est: unknown | 24 h, 15 X | U | 3 |
| R56443 | est: unknown | 24 h, 7 X | U | 3 |
| T70251 | est: unknown | 40, 8 h, 4 X | D | 3 |
| H92205 | est: unknown | 8 h, 4 X | D | 3 |
| T89666 | est: unknown | 8 h, 4 X | D | 3 |
| H13281 | est: unknown | 24 h, 15 X | D | 3 |
| R60741 | est: unknown | 8 h, 4 X | D | 3 |
| H16597 | est: unknown | 24 h, 4 X | D | 3 |
| R40403 | est: unknown | 24 h, 6 X | D | 3 |
| H78404 | est: unknown | 8 h, 4 X | D | 3 |
| T48692 | est: unknown | 8 h, 24 h, 6 X | D | 1 |
| H40677 | est: unknown | 8 h, 6 X | D | 3 |
| H86071 | est: homology to mouse AF003234 | 8 h, 5 X | D | 3 |

We claim:

1. A method of determining the stage of disease caused by HCMV infection, comprising the step of:

determining expression levels in a first human cell sample of a set of genes comprising M24594, Interferon stimulated genes 54K; M87434, 71 kDa 2'5' oligoadenylate synthetase; X02875, (2'-5') oligo A synthetase E (1.8 kb RNA); X02874, (2'-5') oligo A synthetase E (1.6kb RNA); M87284, 69 kDa 2'5' oligoadenylate synthetase; X02530, gamma-interferon inducible early response gene; L05072 Interferon regulatory factor 1 (IRF-1); X5949, Interferon regulatory factor 2 (IRF-2); X67325, Interferon-alpha inducible gene, p27 gene; H05300, Interferon-induced guanylate-binding protein 1; M55542, guanylate binding protein isoform II; D31887, KIAA0062 (cig 19); X88220, interferon inducible gene staf50; X02492, interferon-induced protein 6-16; R34698, interferon-inducible protein 9-27; M13755, interferon-induced 17 kDa/15 kDa protein; M28622, interferon beta; X17668, indoleamine 2,3-dioxygenase; M33882, MxA; M30818, MxB; X56841, HLA-E gene; T50250, est: homo to U51904, mouse IFN α-treated mRNA; M60618, nuclear autoantigen Sp100; M73778, PML-1; R39857, est=X97630—serine/threonine protein kinase EMK; H02889, est=Y11366 IMPA gene; U25994, cell death protein (RIP protein kinase); D21209, protein tyrosine phosphatase (PTP-BAS type 1); X77278, HYL tyrosine kinase; R60908, est=X74764—receptor protein tyrosine kinase; H65441, est=U78027, L35265—Bruton's tyrosine kinase; and X16416, proto-oncogene tyrosine-protein kinase (abl), wherein the first human cell sample consists essentially of HCMV-infected cells of a patient infected with HCMV, wherein the expression levels of one or more genes of the set of genes correlates with stage of disease progression of the HCMV infection; and determining a stage of disease progression based on the expression levels.

2. A method of determining the extent of tissue damage caused by HCMV infection, comprising the step of:

determining expression levels in a first human cell sample of a set of genes comprising M24594, Interferon stimulated genes 54K; M87434, 71 kDa 2'5' oligoadenylate synthetase; X02875, (2'-5') oligo A synthetase E (1.8 kb RNA); X02874, (2'-5') oligo A synthetase E (1.6 kb RNA); M87284, 69 kDa 2'5' oligoadenylate synthetase; X02530, gamma-interferon inducible early response gene; L05072 Interferon regulatory factor 1 (JRF-1); X15949, Interferon regulatory factor 2 (IRF-2); X67325, Interferon-alpha inducible gene, p27 gene; H05300, Interferon-induced guanylate-binding protein 1; M55542, guanylate binding protein isoform II; D31887, KIAA0062 (cig 19); X88220, interferon inducible gene staf50; X02492, interferon-induced protein 6-16; R34698, interferon-inducible protein 9-27; M13755, interferon-induced 17 kDa/15 kDa protein; M28622, interferon beta; X17668, indoleamine 2,3-dioxygenase; M33882, MxA; M30818, MxB; X56841, HLA-E gene; T50250, est: homo to U51904, mouse IFN α-treated mRNA; M60618, nuclear autoantigen Sp100; M73778, PML-1; R39857, est=X97630—serine/threonine protein kinase EMK; H02889, est=Y11366 IMPA gene; U25994, cell death protein (RIP protein kinase); D21209, protein tyrosine phosphatase (PTP-BAS type 1); X77278, HYL tyrosine kinase; R60908, est=X74764—receptor protein tyrosine kinase; H65441, est U78027, L35265—Bruton's tyrosine kinase; and X16416, proto-oncogene tyrosine-protein kinase (abl), wherein the first human cell sample consists essentially of HCMV-infected cells of a patient infected with HCMV, wherein the expression levels of one or more genes in the set correlates with extent of tissue damage caused by the HCMV infection; and determining the extent of tissue damage based on the expression levels.

3. A method for screening to identify candidate drugs for preventing disease symptoms caused by HCMV, comprising the steps of:

contacting human cells with HCMV and a test agent;

determining expression levels of a set of genes comprising M24594, Interferon stimulated genes 54K; M87434, 71 kDa 2'5' oligoadenylate synthetase; X02875, (2'-5') oligo A synthetase E (1.8 kb RNA); X02874, (2'-5') oligo A synthetase E (1.6kb RNA); M87284, 69 kDa 2'5' oligoadenylate synthetase; X02530, gamma-interferon inducible early response gene; L05072 Interferon regulatory factor 1 (IRF-1); X15949, Interferon regulatory factor 2 (IRF-2); X67325, Interferon-alpha inducible gene, p27 gene; H05300, Interferon-induced guanylate-binding protein 1; M55542, guanylate binding protein isoform II; D31887, KIAA0062 (cig 19); X88220, interferon inducible gene staf50; X02492, interferon-induced protein 6-16; R34698, interferon-inducible protein 9-27; M13755, interferon-induced 17 kDaIl5 kDa protein; M28622, interferon beta; X17668, in doleamine 2,3- dioxygenase; M33882, MxA; M30818, MxB; X56841, HLA-E gene; T50250, est: homo to U51904, mouse IFN α-treated mRNA; M60618, nuclear autoantigen Sp100; M73778, PML-1; R39857, est=X97630—serine/threonine protein kinase EMK; H02889, est=Y11366 IMPA gene; U25994, cell death protein (RIP protein kinase); D21209, protein tyrosine phosphatase (PTP-BAS type 1); X77278, HYL tyrosine kinase; R60908, est=X74764—receptor protein tyrosine kinase; H65441, est=U78027, L35265—Bruton's tyrosine kinase; and X16416, proto-oncogene tyrosine-protein kinase (abl);

identifying a test agent as a candidate drug if the test agent causes the human cells to express one or more genes of the set of genes at a level at which the human cells express the one or more genes in the absence of HCMV.

4. The method of claim 1, 2, or 3 wherein one or more genes of the set of genes are induced or repressed to a level which is at least two-fold different than the level of expression in the absence of HCMV.

5. The method of claim 1, 2, or 3 wherein one or more genes of the set of genes are induced or repressed to a level which is at least four-fold different than the level of expression in the absence of HCMV.

6. The method of claim 1, 2, or 3 wherein one or more genes of the set of genes are induced or repressed to a level which is at least eight-fold different than the level of expression in the absence of HCMV.

7. The method of claim 1, 2, or 3 wherein one or more genes of the set of genes are induced or repressed to a level which is at least ten-fold different than the level of expression in the absence of HCMV.

8. A The method of claim 1, 2, or 3 wherein one or more genes of the set of genes are induced or repressed to a level which is at least fifteen-fold different than the level of expression in the absence of HCMV.

9. The method of claim 1, 2, or 3 in which the step of determining expression levels is performed by measuring amounts of mRNA expressed by the set of genes.

10. The method of claim 1, 2, or 3 in which the step of determining expression levels is performed by measuring amounts of protein expressed by the set of genes.

11. The method of claim 1, 2, or 3 in which the step of determining expression levels is performed using an array of oligonucleotides.

12. The method of claim 1, 2, or 3 in which the step of determining expression levels is performed using serial analysis of gene expression.

13. The method of claim 1, 2, or 3 in which the step of determining expression levels is performed using hybridization of nucleic acids on a solid support.

14. The method of claim 1, 2, or 3 in which the step of determining expression levels is performed using cDNA which is made using mRNA collected from the human cells as a template.

15. The method of claim 1, 2, or 3 in which a fluorescent label is used to determine expression levels.

16. The method of claim 1, 2, or 3 in which the set of genes comprises at least 150 genes.

17. The method of claim 1, 2, or 3 in which the set of genes comprises at least 50 genes.

18. The method of claim 1, 2, or 3 in which the set of genes comprises at least 100 genes.

19. The method of claim 1, 2, or 3 in which the set of genes comprises at least 200 genes.

20. The method of claim 1, 2, or 3 in which the set of genes comprises at least 250 genes.

21. The method of claim 1, 2, or 3 in which the set of genes comprises at least 500 genes.

22. The method of claim 1, 2, or 3 in which the set of genes comprises at least 1000 genes.

23. The method of claim 1, 2, or 3 in which the human cells are fibroblasts.

24. The method of claim 1, 2, or 3 in which the human cells are lymphocytes.

25. The method of claim 1, 2, or 3 in which the human cells are epithelial cells.

26. The method of claim 1, 2, or 3 in which the human cells are lung epithelial cells.

27. The method of claim 1, 2, or 3 in which the human cells are neuronal cells.

28. The method of claim 1 or 2 further comprising the step of:

determining expression levels in a second human cell sample of said genes, wherein the second human cell sample comprises cells of said patient, wherein the second human cell sample consists essentially of uninfected cells, wherein the first and the second human cell sample comprise the same cell type;

comparing the expression levels determined in the first and the second human cell samples.

29. The method of claim 1 or 2 wherein the expression levels determined in the first human cell sample are compared to expression levels determined for a reference sample of uninfected human cells of the same cell type.

* * * * *

UNITED STATES PATENT AND TRADEMARK OFFICE
CERTIFICATE OF CORRECTION

PATENT NO. : 6,936,416 B2
APPLICATION NO. : 09/950024
DATED : August 30, 2005
INVENTOR(S) : Zhu et al.

It is certified that error appears in the above-identified patent and that said Letters Patent is hereby corrected as shown below:

On Page 2 of the cover page, References Cited section (56), Other publications:
    In the last reference of the second column:
    Please replace "Apr. 1996" with --Apr. 1998--

In Column 37, Claim 1, Line 30:
    Please replace "X5949," with --X15949,--

In Column 37, Claim 2, Line 67:
    Please replace "(JRF-1);" with --(IRF-1);--

In Column 38, Claim 2, Line 37:
    Please replace "est U78027" with --est=U78027--

In Column 38, Claim 3, Line 65:
    Please replace "kDaI15" with --kDa/15--

In Column 38, Claim 3, Line 67:
    Please replace "in doleamine" with --indoleamine--

Signed and Sealed this

Nineteenth Day of December, 2006

JON W. DUDAS
*Director of the United States Patent and Trademark Office*

SEQUENCE LISTING

<160> NUMBER OF SEQ ID NOS: 1

<210> SEQ ID NO 1
<211> LENGTH: 63
<212> TYPE: DNA
<213> ORGANISM: Artificial Sequence
<220> FEATURE:
<223> OTHER INFORMATION: synthetic sequence

<400> SEQUENCE: 1

```
ggccagtgaa ttgtaatacg actcactata gggaggcggt tttttttttt tttttttttt      60
ttt                                                                    63
```